(12) United States Patent
Gong

(10) Patent No.: US 11,774,534 B2
(45) Date of Patent: Oct. 3, 2023

(54) SYSTEMS AND METHODS FOR MAGNETIC RESONANCE IMAGING

(71) Applicant: SHANGHAI UNITED IMAGING HEALTHCARE CO., LTD., Shanghai (CN)

(72) Inventor: Xiaomao Gong, Shanghai (CN)

(73) Assignee: SHANGHAI UNITED IMAGING HEALTHCARE CO., LTD., Shanghai (CN)

(*) Notice: Subject to any disclaimer, the term of this patent is extended or adjusted under 35 U.S.C. 154(b) by 0 days.

(21) Appl. No.: 17/653,865

(22) Filed: Mar. 7, 2022

(65) Prior Publication Data

US 2022/0196773 A1 Jun. 23, 2022

Related U.S. Application Data

(63) Continuation of application No. 16/861,332, filed on Apr. 29, 2020, now Pat. No. 11,269,035.

(30) Foreign Application Priority Data

Apr. 30, 2019 (CN) .......................... 201910358319.4

(51) Int. Cl.
*G01V 3/00* (2006.01)
*G01R 33/56* (2006.01)
(Continued)

(52) U.S. Cl.
CPC .......... *G01R 33/5608* (2013.01); *A61B 5/055* (2013.01); *G01R 33/482* (2013.01);
(Continued)

(58) Field of Classification Search
CPC .............. G01R 33/3415; G01R 33/543; G01R 33/5659; G01R 33/36; A61B 5/055
(Continued)

(56) References Cited

U.S. PATENT DOCUMENTS 5,561,370 A 10/1996 Fuderer
5,570,019 A 10/1996 Moonen et al.
(Continued)

FOREIGN PATENT DOCUMENTS

CN 1589410 A * 3/2005 ......... G01R 33/3854
CN 200976043 Y 11/2007
(Continued)

OTHER PUBLICATIONS

AU 627483 B2 (Leunbach) (Year: 1992).*
(Continued)

*Primary Examiner* — Walter L Lindsay, Jr.
*Assistant Examiner* — Frederick Wenderoth
(74) *Attorney, Agent, or Firm* — METIS IP LLC

(57) ABSTRACT

A method for magnetic resonance imaging (MRI) may include cause, based on a pulse sequence, a magnetic resonance (MR) scanner to perform a scan on an object. The pulse sequence may include a steady-state sequence and an acquisition sequence that is different from the steady-state sequence. The steady-state sequence may correspond to a steady-state phase of the scan in which no MR data is acquired. The acquisition sequence may correspond to an acquisition phase of the scan in which MR data of the object is acquired. The method may also include generating one or more images of the object based on the MR data.

20 Claims, 9 Drawing Sheets

(51) Int. Cl.
*G01R 33/54* (2006.01)
*G01R 33/483* (2006.01)
*G01R 33/565* (2006.01)
*A61B 5/055* (2006.01)
*G01R 33/561* (2006.01)
*G01R 33/567* (2006.01)
*G01R 33/48* (2006.01)

(52) U.S. Cl.
CPC ....... *G01R 33/4835* (2013.01); *G01R 33/543* (2013.01); *G01R 33/5613* (2013.01); *G01R 33/5615* (2013.01); *G01R 33/5673* (2013.01); *G01R 33/56509* (2013.01); *G01R 33/56554* (2013.01)

(58) Field of Classification Search
USPC .......................................................... 324/309
See application file for complete search history.

(56) References Cited

U.S. PATENT DOCUMENTS

| | | | |
|---|---|---|---|
| 5,742,163 | A | 4/1998 | Liu et al. |
| 5,751,145 | A | 5/1998 | Shimizu |
| 5,825,185 | A | 10/1998 | Liu et al. |
| 5,830,143 | A | 11/1998 | Mistretta et al. |
| 6,414,487 | B1 | 7/2002 | Anand et al. |
| 6,420,870 | B1 | 7/2002 | Kiefer |
| 8,143,891 | B2 | 3/2012 | Priatna et al. |
| 8,417,005 | B1 | 4/2013 | Martel et al. |
| 8,831,704 | B2 | 9/2014 | Stemmer |
| 8,942,445 | B2 | 1/2015 | Foo et al. |
| 9,872,250 | B2 | 1/2018 | Nicks et al. |
| 10,231,672 | B2 | 3/2019 | Yoshida |
| 2004/0027124 | A1 | 2/2004 | Abe et al. |
| 2009/0302840 | A1* | 12/2009 | Fung ................. G01R 33/5601 |
| 2011/0130644 | A1 | 6/2011 | Stemmer |
| 2012/0146640 | A1 | 6/2012 | Kusahara et al. |
| 2012/0262172 | A1 | 10/2012 | Holmes et al. |
| 2012/0313641 | A1 | 12/2012 | Labadie et al. |
| 2015/0073263 | A1 | 3/2015 | Gdaniec |
| 2015/0091570 | A1 | 4/2015 | Gross et al. |
| 2015/0091572 | A1 | 4/2015 | Gross et al. |
| 2015/0301136 | A1 | 10/2015 | Li et al. |
| 2015/0355301 | A1 | 12/2015 | Zhang |
| 2015/0374237 | A1 | 12/2015 | Hu et al. |
| 2016/0033607 | A1 | 2/2016 | Sun et al. |
| 2016/0131727 | A1* | 5/2016 | Sacolick .............. G01R 33/445 324/318 |
| 2016/0313429 | A1 | 10/2016 | Van Den Brink et al. |
| 2017/0186181 | A1 | 6/2017 | Sakas et al. |
| 2017/0219674 | A1 | 8/2017 | Van Der Kouwe et al. |
| 2018/0092569 | A1* | 4/2018 | Li ......................... A61B 5/055 |
| 2018/0120403 | A1 | 5/2018 | Liu et al. |
| 2018/0149724 | A1 | 5/2018 | Kartäusch et al. |
| 2018/0188343 | A1* | 7/2018 | Liu ....................... A61B 5/055 |
| 2018/0204358 | A1 | 7/2018 | An et al. |

FOREIGN PATENT DOCUMENTS

| | | | | |
|---|---|---|---|---|
| CN | 101647699 | A | | 2/2010 |
| CN | 103961097 | A | | 8/2014 |
| CN | 104181487 | A | | 12/2014 |
| CN | 104569882 | A | | 4/2015 |
| CN | 104644172 | A | | 5/2015 |
| CN | 204500697 | U | * | 7/2015 |
| CN | 104833931 | A | * | 8/2015 ....... G01R 33/34092 |
| CN | 105919593 | A | | 9/2016 |
| CN | 106539584 | A | | 3/2017 |
| CN | 107153169 | A | | 9/2017 |
| CN | 107510458 | A | | 12/2017 |
| CN | 107621616 | A | | 1/2018 |
| CN | 108056820 | A | * | 5/2018 ......... A61B 18/1492 |
| CN | 108514415 | A | | 9/2018 |
| CN | 109143132 | A | | 1/2019 |
| CN | 109613461 | A | | 4/2019 |
| CN | 106646302 | B | | 11/2019 |
| EP | 0185194 | A2 | | 6/1986 |
| EP | 1113288 | A2 | | 7/2001 |
| EP | 2631664 | A1 | | 8/2013 |
| JP | 2001204708 | A | * | 7/2001 |
| JP | 2005152175 | A | * | 6/2005 |
| JP | 3967210 | B2 | | 8/2007 |
| JP | 4711732 | B2 | | 6/2011 |
| WO | 2013182967 | A1 | | 12/2013 |

OTHER PUBLICATIONS

First Office Action in Chinese Application No. 201910358319.4 dated Oct. 30, 2020, 16 pages.
The Second Office Action in Chinese Application No. 201910358319.4 dated Jun. 10, 2021, 10 pages.
Peng, Yijun, Research of Segmented K-Space Imaging in MRI, Chinese Outstanding Master's Thesis Full-text Database Information Technology Series, 2009, 64 pages.
International Search Report in PCT/CN2016/085412 dated Sep. 1, 2016, 5 pages.
Written Opinion in PCT/CN2016/085412 dated Sep. 21, 2016, 4 pages.
The Extended European Search Report in European Application No. 16827127.8 dated Jul. 19, 2018, 15 pages.
Julian R. MacLaren et al., A modified view ordering for artifact reduction in MRI, Proceedings of the 29th Annual International Conference of the IEEE EMBS, 2053-2056, 2007.
First Office Action in Chinese Application No. 201510719200.7 dated Jan. 30, 2019, 13 pages.

* cited by examiner

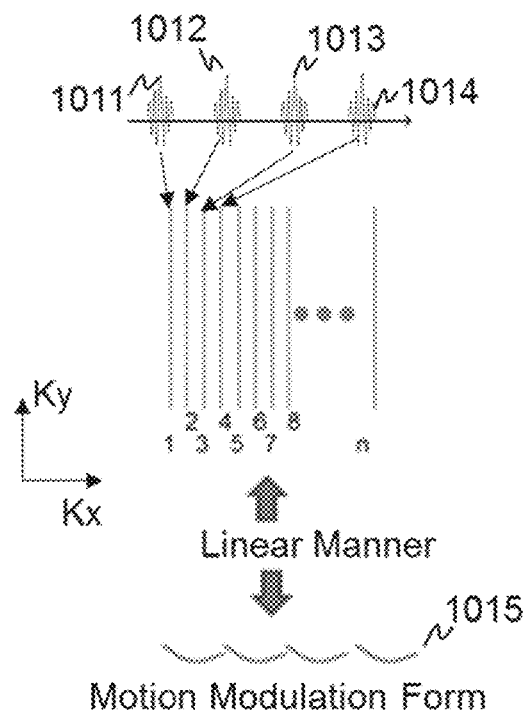
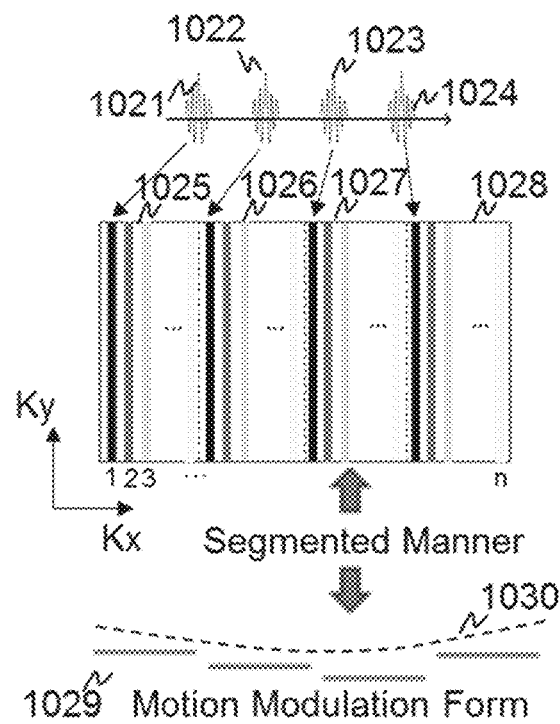
FIG. 10A
FIG. 10B
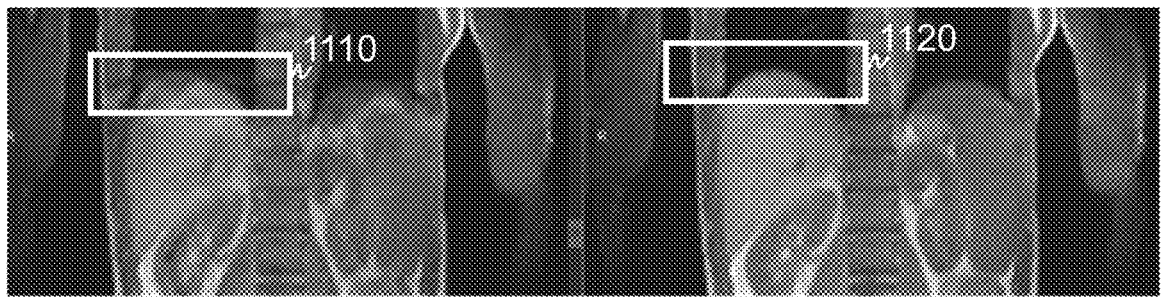
FIG. 11A
FIG. 11B

SYSTEMS AND METHODS FOR MAGNETIC RESONANCE IMAGING

CROSS-REFERENCE TO RELATED APPLICATIONS

This application is a continuation of U.S. application Ser. No. 16/861,332, filed on Apr. 29, 2020, which claims priority to Chinese Patent Application No. 201910358319.4 filed on Apr. 30, 2019, the contents of which are incorporated herein by reference.

TECHNICAL FIELD

The present disclosure generally relates to imaging, and in particular, to systems and methods for magnetic resonance imaging (MRI).

BACKGROUND

Magnetic resonance imaging (MRI) is a widely used medical technique which may produce images of an object by exploiting a powerful magnetic field and radio frequency (RF) techniques. During an MRI process, the acquired signals may be processed and filled into k-space, then data in the k-space may be transformed to reconstruct MRI images. A physiological motion of the object, such as respiratory motion, cardiac motion, etc., may cause motion artifacts in the reconstructed MRI images, which reduces the quality of the reconstructed MRI images. Therefore, it is desirable to provide systems and/or methods for MRI to suppress the motion artifacts effectively and to make the reconstructed MRI images clearer.

SUMMARY

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

According to a first aspect of the present disclosure, a system for magnetic resonance imaging (MRI) may include one or more storage devices and one or more processors configured to communicate with the one or more storage devices. The one or more storage devices may include a set of instructions. When the one or more processors executing the set of instructions, the one or more processors may be directed to perform one or more of the following operations. The one or more processors may cause, based on a pulse sequence, a magnetic resonance (MR) scanner to perform a scan on an object. The pulse sequence may include a steady-state sequence and an acquisition sequence that is different from the steady-state sequence. The steady-state sequence may correspond to a steady-state phase of the scan in which no MR data is acquired. The acquisition sequence may correspond to an acquisition phase of the scan in which MR data of the object is acquired. The one or more processors may generate one or more images of the object based on the MR data.

In some embodiments, the acquisition sequence may include an excitation pulse, a slice selection gradient, a phase encoding gradient, and a readout gradient. The steady-state sequence may include the excitation pulse and the slice selection gradient.

In some embodiments, the acquisition sequence may include a first dephasing gradient. The steady-state sequence may include a second dephasing gradient.

In some embodiments, the steady-state sequence may be free of at least one of any phase encoding gradient or any readout gradient.

In some embodiments, a zeroth moment of the second dephasing gradient may be equal to a zeroth moment of the first dephasing gradient.

In some embodiments, a duration of a first dephasing period of the first dephasing gradient may be shorter than a duration of a second dephasing period of the second dephasing gradient.

In some embodiments, a maximum amplitude of the first dephasing gradient may be greater than a maximum amplitude of the second dephasing gradient.

In some embodiments, a slew rate of the first dephasing gradient may be greater than a slew rate of the second dephasing gradient.

In some embodiments, the second dephasing gradient or the first dephasing gradient may be applied along at least one of a direction of the slice selection gradient, a direction of the phase encoding gradient, or a direction of the readout gradient.

In some embodiments, the scan may be performed during one or more cycles of a physiological motion of the object.

In some embodiments, the causing, based on the pulse sequence, the MR scanner to perform a scan on an object may include the following operations. The one or more processors may acquire a physiological signal of the physiological motion of the object. The one or more processors may evaluate a trigger condition based on the physiological signal. The one or more processors may cause the MR scanner to operate based on the evaluation of the trigger condition.

In some embodiments, the causing the MR scanner to operate based on the evaluation of the trigger condition may include the following operations. In response to determining that the trigger condition is not satisfied, the one or more processors may cause the MR scanner to operate based on the steady-state sequence.

In some embodiments, the causing the MR scanner to operate based on the evaluation of the trigger condition may include the following operations. In response to determining that the trigger condition is satisfied, the one or more processors may cause the MR scanner to operate based on the acquisition sequence.

In some embodiments, the one or more cycles of the physiological motion may include multiple cycles of the physiological motion. Acquiring the MR data may include the following operations. The one or more processors may divide k-space into a plurality of regions based on a count of a plurality of echoes acquired in each of the multiple cycles. The plurality of echoes acquired in each of the multiple cycles may correspond to a portion of the MR data acquired in the each of the multiple cycles. The one or more processors may acquire the MR data by filling the echoes acquired in the multiple cycles into the plurality of regions of the k-space based on the acquisition sequence. The echoes acquired in different cycles of the multiple cycles may be filled in same regions of the plurality of regions. The echoes acquired in a same cycle of the multiple cycles may be filled in different regions of the plurality of regions.

In some embodiments, each of the plurality of echoes acquired in each of the multiple cycles may correspond to a motion phase of the physiological motion of the object. Echoes corresponding to a same motion phase may be filled into a same region of the plurality of regions.

In some embodiments, the steady-state phase and the acquisition phase may be periodically distributed in each of the multiple cycles.

In some embodiments, the steady-state sequence and the acquisition sequence may correspond to a repetition time (TR) of the scan. The steady-state sequence and the acquisition sequence may correspond to different magnetic field gradients.

According to another aspect of the present disclosure, a method for MRI may include one or more of the following operations. One or more processors may cause, based on a pulse sequence, a magnetic resonance (MR) scanner to perform a scan on an object. The pulse sequence may include a steady-state sequence and an acquisition sequence that is different from the steady-state sequence. The steady-state sequence may be used to maintain a steady-state spin magnetization in the object. The steady-state sequence may correspond to a steady-state phase of the scan. The acquisition sequence may correspond to an acquisition phase of the scan in which MR data of the object is acquired. The one or more processors may generate one or more images of the object based on the MR data.

According to yet another aspect of the present disclosure, a system for MRI may include a control module configured to cause, based on a pulse sequence, a magnetic resonance (MR) scanner to perform a scan on an object. The pulse sequence may include a steady-state sequence and an acquisition sequence that is different from the steady-state sequence. The steady-state sequence may be used to maintain a steady-state spin magnetization in the object. The steady-state sequence may correspond to a steady-state phase of the scan. The acquisition sequence may correspond to an acquisition phase of the scan in which MR data of the object is acquired. The system may also include an image generation module configured to generate one or more images of the object based on the MR data.

According to yet another aspect of the present disclosure, a non-transitory computer readable medium may comprise at least one set of instructions. The at least one set of instructions may be executed by one or more processors of a computing device. The one or more processors may cause, based on a pulse sequence, a magnetic resonance (MR) scanner to perform a scan on an object. The pulse sequence may include a steady-state sequence and an acquisition sequence that is different from the steady-state sequence. The steady-state sequence may be used to maintain a steady-state spin magnetization in the object. The steady-state sequence may correspond to a steady-state phase of the scan. The acquisition sequence may correspond to an acquisition phase of the scan in which MR data of the object is acquired. The one or more processors may generate one or more images of the object based on the MR data.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIG. 10A is a schematic diagram illustrating an exemplary linear manner in which echoes are filled into k-space based on a Cartesian trajectory according to some embodiments of the present disclosure;

FIG. 10B is a schematic diagram illustrating an exemplary segmented manner in which echoes are filled into k-space based on a Cartesian trajectory according to some embodiments of the present disclosure;

FIG. 11A is a schematic diagram illustrating an exemplary liver image generated based on MR data filled into k-space in a linear manner according to some embodiments of the present disclosure; and FIG. 11B is a schematic diagram illustrating an exemplary liver image generated based on MR data filled into k-space in a segmented manner according to some embodiments of the present disclosure.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "unit," "module," and/or "block" used herein are one method to distinguish different components, elements, parts, section or assembly of different levels in ascending order. However, the terms may be displaced by another expression if they achieve the same purpose.

Figure 3:
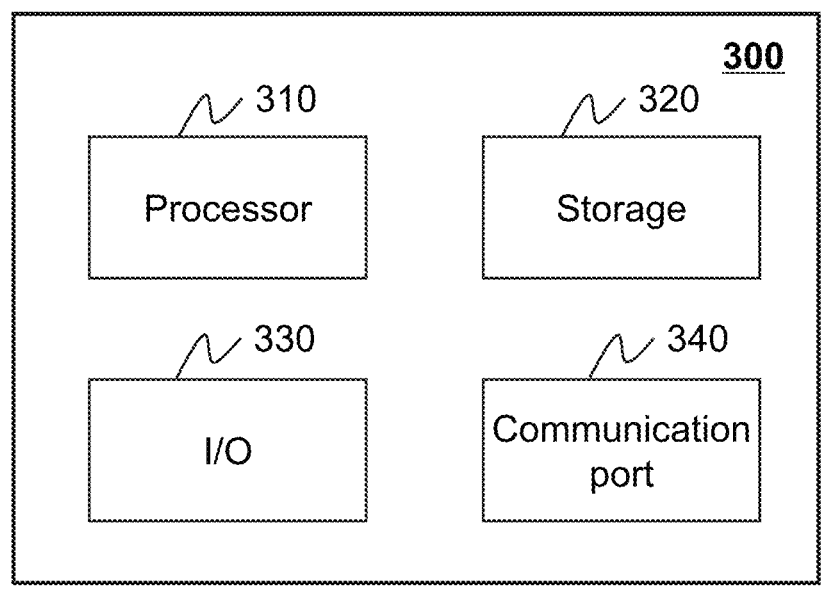
FIG. 3 is a schematic diagram illustrating exemplary hardware and/or software components of a computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 310 as illustrated in FIG. 3) may be provided on a computer readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included of connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

In the present disclosure, terms "steady sequence," "steady state sequence," and "steady-state sequence" may be used interchangeably. Terms "steady phase," "steady state phase," and "steady-state phase" may be used interchangeably.

Provided herein are systems and components for medical imaging and/or medical treatment. In some embodiments, the medical system may include an imaging system. The imaging system may include a single modality imaging system and/or a multi-modality imaging system. The single modality imaging system may include, for example, a magnetic resonance imaging (MRI) system. Exemplary MRI systems may include a superconducting magnetic resonance imaging system, a non-superconducting magnetic resonance imaging system, etc. The multi-modality imaging system may include, for example, a computed tomography-magnetic resonance imaging (MRI-CT) system, a positron emission tomography-magnetic resonance imaging (PET-MRI) system, a single photon emission computed tomography-magnetic resonance imaging (SPECT-MRI) system, a digital subtraction angiography-magnetic resonance imaging (DSA-MRI) system, etc. In some embodiments, the medical system may include a treatment system. The treatment system may include a treatment plan system (TPS), image-guided radiotherapy (IGRT) system, etc. The image-guided radiotherapy (IGRT) system may include a treatment device and an imaging device. The treatment device may include a linear accelerator, a cyclotron, a synchrotron, etc., configured to perform a radiotherapy on a subject. The treatment device may include an accelerator of species of particles including, for example, photons, electrons, protons, or heavy ions. The imaging device may include an MRI scanner, a CT scanner (e.g., cone beam computed tomography (CBCT) scanner), a digital radiology (DR) scanner, an electronic portal imaging device (EPID), etc.

An aspect of the present disclosure relates to systems and methods for MRI. A gating technique may be used to perform an MRI scan of an object based on physiological signals of a physiological motion of the object. According to the gating technique, during one or more cycles of the physiological motion, the scan may include an acquisition phase in which MR data is acquired and a steady-state phase in which no MR data of the object is acquired. In the steady-state phase, if an MRI scanner operates to generate high noise, the comfort level of the object may be reduced, thereby affecting the physiological motion of the object (e.g., inducing unstable physiological motion of the object). Unstable physiological motion may make the physiological signals acquired in each of the one or more cycles inconsistent, which may affect the stability of the gating technique and may cause motion artifacts in one or more images obtained based on the MR data so acquired. In some embodiments of the present disclosure, a pulse sequence including a steady-state sequence and an acquisition sequence may be employed. The MRI scanner may operate based on the steady sequence in the steady-state phase. The steady sequence may be free of any readout gradient and/or any phase encoding gradient, which may reduce the noise generated by the MRI scanner in the steady-state phase. The MRI scanner may operate based on an acquisition sequence in the acquisition phase. The acquisition phase may include a first dephasing gradient to reduce or remove the dephasing of the procession of the protons of the object caused by non-uniformity of the main magnetic field applied by the MRI scanner. The steady sequence may include a second dephasing gradient to reduce or remove the dephasing of the procession of the protons. An effective amplitude of the second dephasing gradient may be smaller than an effective amplitude of the first dephasing gradient, and/or a slew rate of the second dephasing gradient may be smaller than a slew rate of the first dephasing gradient, which may reduce the noise generated by the MRI scanner in the steady-state phase.

In order to suppress motion artifacts in one or more images, according to some embodiments of the present disclosure, echoes may be filled into k-space in a segmented manner. In the segmented manner, the k-space may be divided into a plurality of regions. The echoes acquired in different cycles of the physiological motion of the object may be filled in same regions of the plurality of regions. The echoes acquired in a same cycle may be filled in different regions of the plurality of regions. The echoes corresponding to a same motion phase of the physiological motion may be filled into a same region of the plurality of regions. The segmented manner may make a motion modulation form of the k-space similar to a curve of the physiological motion corresponding to the acquisition phase of one cycle of the physiological motion, which may reduce the motion artifacts in one or more images obtained based on MR data (e.g., echoes, K-space data) so acquire.

Figure 1:
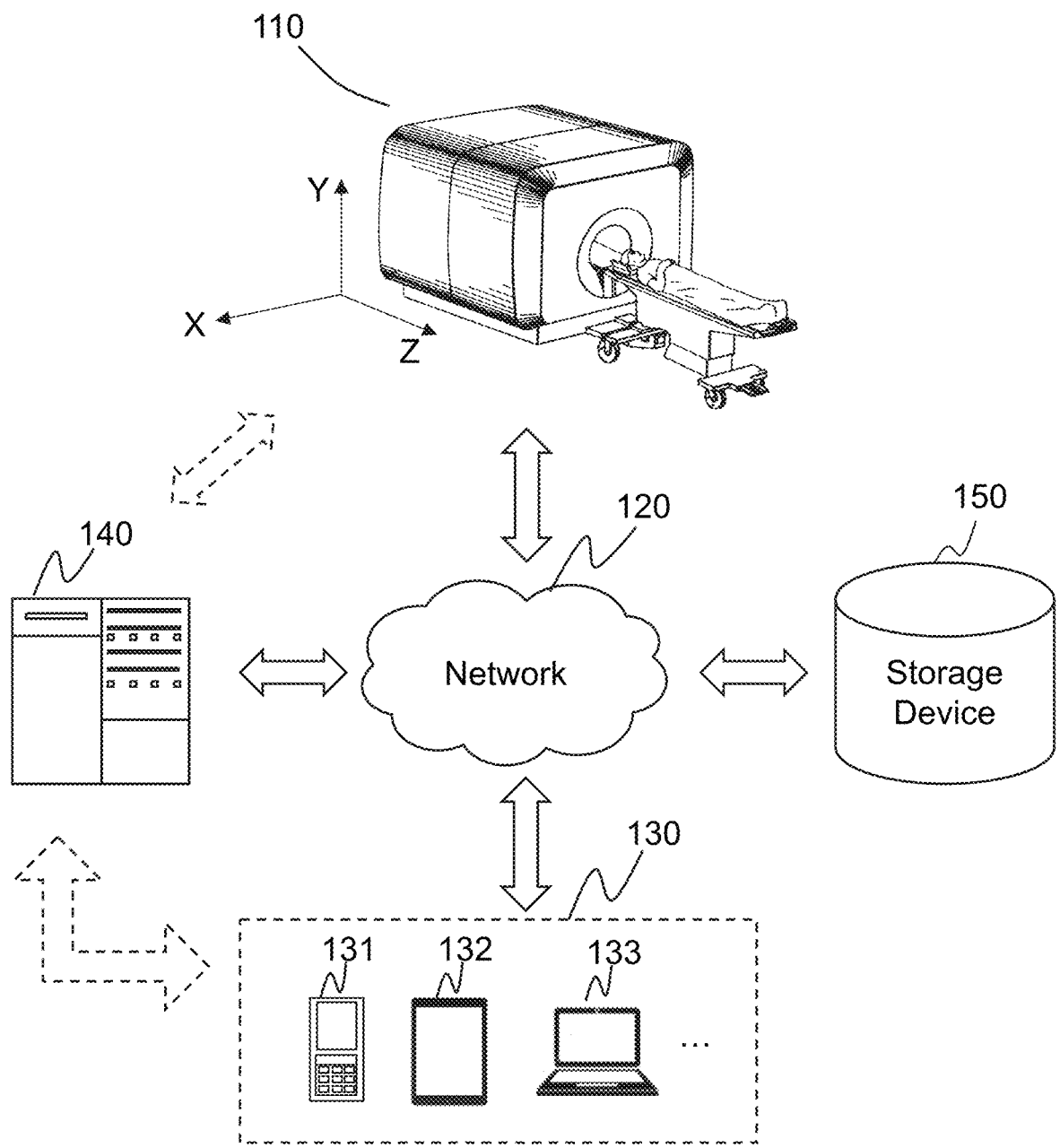
FIG. 1 is a schematic diagram illustrating an exemplary MRI system according to some embodiments of the present disclosure.

FIG. 1 is a schematic diagram illustrating an exemplary MRI system 100 according to some embodiments of the present disclosure. As illustrated, the MRI system 100 may include a scanner 110, a network 120, a user device 130, a processing device 140, and a storage device 150. The components of the MRI system 100 may be connected in one or more of various ways. Mere by way of example, as illustrated in FIG. 1, the scanner 110 may be connected to the processing device 140 through the network 120. As another example, the scanner 110 may be connected to the processing device 140 directly (as indicated by the bi-directional arrow in dotted lines linking the scanner 110 and the processing device 140). As a further example, the storage device 150 may be connected to the processing device 140 directly or through the network 120. As still a further example, the user device 130 (e.g., 131, 132, 133, etc.) may be connected to the processing device 140 directly (as indicated by the bi-directional arrow in dotted lines linking the user device 130 and the processing device 140) or through the network 120.

The scanner 110 may scan an object located within its detection region and generate a plurality of imaging data relating to the object. In the present disclosure, "subject" and "object" are used interchangeably. Mere by way of example, the object may include a patient, a man-made object, etc. As another example, the object may include a specific portion, organ, and/or tissue of a patient. For example, the object may include head, brain, neck, body, shoulder, arm, thorax, cardiac, stomach, blood vessel, soft tissue, knee, feet, or the like, or any combination thereof.

In some embodiments, the scanner 110 may include an MRI scanner, a multi-modality device, etc. Exemplary multi-modality device may include an MRI-CT device, a PET-MRI device, etc. In some embodiments, the MRI scanner may be a close-bore scanner or an open-bore scanner. In the present disclosure, the X axis, the Y axis, and the Z axis shown in FIG. 1 may form an orthogonal coordinate system. The X axis and the Z axis shown in FIG. 1 may be horizontal, and the Y axis may be vertical. As illustrated, the positive X direction along the X axis may be from the right side to the left side of the scanner 110 seen from the direction facing the front of the scanner 110; the positive Y direction along the Y axis shown in FIG. 1 may be from the lower part to the upper part of the scanner 110; the positive Z direction along the Z axis shown in FIG. 1 may refer to a direction in which the object is moved out of the scanning channel (or referred to as the bore) of the scanner 110. More description of the scanner 110 may be found elsewhere in the present disclosure. See, e.g., FIG. 2 and the description thereof.

The network 120 may include any suitable network that can facilitate the exchange of information and/or data for the MRI system 100. In some embodiments, one or more components of the MRI system 100 (e.g., the scanner 110, the user device 130, the processing device 140, or the storage device 150) may communicate information and/or data with one or more other components of the MRI system 100 via the network 120. For example, the processing device 140 may obtain magnetic resonance (MR) data (also referred to as MR signals, echo signals, or echo data) from the scanner 110 via the network 120. As another example, the user device 130 and/or the storage device 150 may obtain one or more images from the processing device 140. In some embodiments, the network 120 may be any type of wired or wireless network, or a combination thereof. The network 120 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the MRI system 100 may be connected to the network 120 to exchange data and/or information.

The user device 130 may include a mobile device 131, a tablet computer 132, a laptop computer 133, a desktop computer (not shown), a workstation (not shown), or the like, or any combination thereof. In some embodiments, the mobile device 131 may include a smart home device, a wearable device, a smart mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a smart bracelet, smart footgear, a pair of smart glasses, a smart helmet, a smart watch, smart clothing, a smart backpack, a smart accessory, or the like, or any combination thereof. In some embodiments, the smart mobile device may include a smartphone, a personal digital assistant (PDA), a gaming device, a navigation device, a point of sale (POS) device, or the like, or any combination thereof. In some embodiments, the virtual reality device and/or the augmented reality device may include a virtual reality helmet, a virtual reality glass, a virtual reality patch, an augmented reality helmet, an augmented reality glass, an augmented reality patch, or the like, or any combination thereof. For example, the virtual reality device and/or the augmented reality device may include a Google™ Glass, an Oculus Rift, a Hololens, a Gear VR, etc. In some embodiments, the user device 130 may remotely operate the scanner 110 and/or the processing device 140. In some embodiments, the user device 130 may operate the scanner 110 and/or the processing device 140 via a wireless connection. In some embodiments, the user device 130 may receive information and/or instructions inputted by a user, and send the received information and/or instructions to the scanner 110 or to the processing device 140 via the network 120. For example, a user (e.g., a doctor, a technician, or an engineer, etc.) of the MRI system 100 may set a scan protocol though the user device 130. The user device 130 may send the scan protocol to the processing device 140 to direct the processing device 140 to cause the scanner 110 (e.g., the MRI scanner) to operate according to the scan protocol. In some embodiments, the user device 130 may receive data and/or information from the processing device 140 and/or the storage device 150. For example, the user device 130 may obtain one or more images from the processing device 140 and/or the storage device 150.

The processing device 140 may process data and/or information obtained from the scanner 110, the user device 130, and/or the storage device 150. For example, the processing device 140 may obtain MR data from the scanner 110 and determine one or more images based on the MR data. As another example, the processing device 140 may receive one or more instructions from the user device 130 and cause the scanner 110 to operate according to the one or more instructions. In some embodiments, the processing device 140 may be a single server, or a server group. The server group may be centralized or distributed. In some embodiments, the processing device 140 may be local or remote. For example, the processing device 140 may access information and/or data stored in or acquired by the scanner 110, the user device 130, and/or the storage device 150 via the network 120. As another example, the processing device 140 may be directly connected to the scanner 110 (as illustrated by the bidirectional arrow in dashed lines connecting the processing device 140 and the scanner 110 in FIG. 1), the user device 130 (as illustrated by the bidirectional arrow in dashed lines connecting the processing device 140 and the user device 130 in FIG. 1), and/or the storage device 150 to access stored or acquired information and/or data. In some embodiments, the processing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 140 may be implemented on a computing device 300 having one or more components illustrated in FIG. 3 in the present disclosure.

The storage device 150 may store data and/or instructions. In some embodiments, the storage device 150 may include a database, a picture archiving and communication system, a file system, or the like, or any combination thereof. In some embodiments, the storage device 150 may store data obtained from the scanner 110, the user device 130 and/or the processing device 140. For example, the storage device 150 may store MR data acquired by the scanner 110. As another example, the storage device 150 may store medical images (e.g., MRI images) generated by the processing device 140 and/or the user device 130. As a further example, the storage device 150 may store preset scan parameters (e.g., preset scan protocols) of the MRI system 100. In some embodiments, the storage device 150 may store data and/or instructions that the processing device 140 may execute or use to perform exemplary methods described in the present disclosure. For example, the storage device 150 may store instructions that the processing device 140 may execute to cause the scanner 110 to acquire MR data based on a pulse sequence including a steady-state sequence and an acquisition sequence. As another example, the storage device 150 may store instructions that the processing device 140 and/or the user device 130 may execute to generate one or more images based on the MR data. In some embodiments, the storage device 150 may include a mass storage device, a removable storage device, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage device 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 120 to communicate with one or more components of the MRI system 100 (e.g., the scanner 110, the processing device 140, the user device 130, etc.). One or more components of the MRI system 100 may access the data or instructions stored in the storage device 150 via the network 120. In some embodiments, the storage device 150 may be directly connected to or communicate with one or more components of the MRI system 100 (e.g., the scanner 110, the processing device 140, the user device 130, etc.). In some embodiments, the storage device 150 may be part of the processing device 140.

In some embodiments, the MRI system 100 may further include one or more power supplies (not shown in FIG. 1) connected to one or more components of the MRI system 100 (e.g., the scanner 110, the processing device 140, the user device 130, the storage device 150, etc.).

Figure 2:
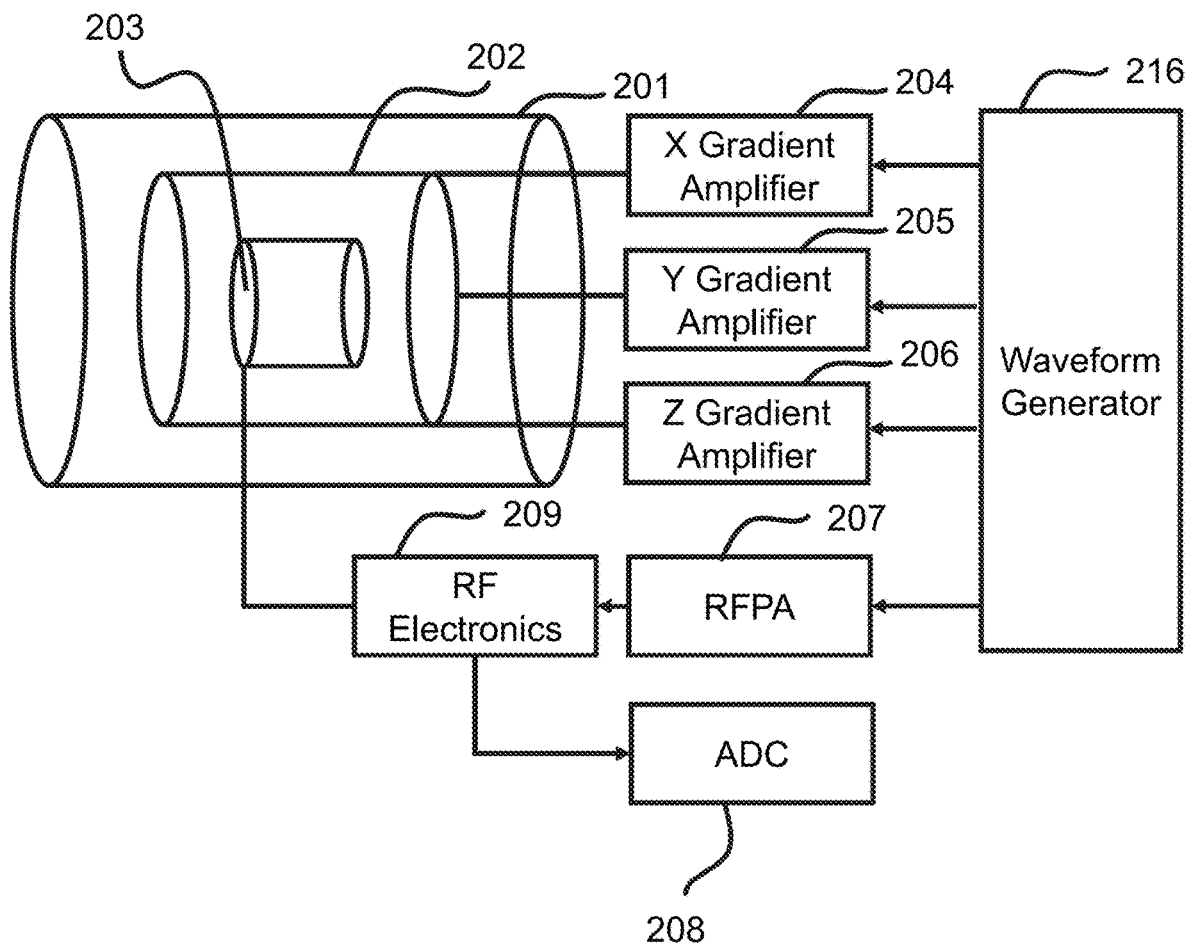
FIG. 2 is a schematic diagram illustrating an exemplary MRI scanner according to some embodiments of the present disclosure.

FIG. 2 is a schematic diagram illustrating an exemplary MRI scanner according to some embodiments of the present disclosure. As illustrated, the main magnet 201 may generate a first magnetic field (or referred to as a main magnetic field) that may be applied to an object (also referred to as a subject) exposed inside the field. The main magnet 201 may include a resistive magnet or a superconductive magnet that both need a power supply (not shown) for operation. Alternatively, the main magnet 201 may include a permanent magnet. The main magnet 201 may include a bore that the object is placed within. The main magnet 201 may also control the homogeneity of the generated main magnetic field. Some shim coils may be in the main magnet 201. The shim coils placed in the gap of the main magnet 201 may compensate for the inhomogeneity of the magnetic field of the main magnet 201. The shim coils may be energized by a shim power supply.

Gradient coils 202 may be located inside the main magnet 201. The gradient coils 202 may generate a second magnetic field (or referred to as a gradient field, including gradient fields Gx, Gy, and Gz). The second magnetic field may be superimposed on the main field generated by the main magnet 201 and distort the main field so that the magnetic orientations of the protons of an object may vary as a function of their positions inside the gradient field, thereby encoding spatial information into MR signals generated by the object being imaged. The gradient coils 202 may include X coils (e.g., configured to generate the gradient field Gx corresponding to the X direction), Y coils (e.g., configured to generate the gradient field Gy corresponding to the Y direction), and/or Z coils (e.g., configured to generate the gradient field Gz corresponding to the Z direction) (not shown in FIG. 2). In some embodiments, the Z coils may be designed based on circular (Maxwell) coils, while the X coils and the Y coils may be designed on the basis of the saddle (Golay) coil configuration. The three sets of coils may generate three different magnetic fields that are used for position encoding. The gradient coils 202 may allow spatial encoding of MR signals for image construction. The gradient coils 202 may be connected with one or more of an X gradient amplifier 204, a Y gradient amplifier 205, or a Z gradient amplifier 206. One or more of the three amplifiers may be connected to a waveform generator 216. The waveform generator 216 may generate gradient waveforms that are applied to the X gradient amplifier 204, the Y gradient amplifier 205, and/or the Z gradient amplifier 206. An amplifier may amplify a waveform. An amplified waveform may be applied to one of the coils in the gradient coils 202 to generate a magnetic field in the X axis, the Y axis, or the Z axis, respectively. The gradient coils 202 may be designed for either a close-bore MRI scanner or an open-bore MRI scanner. In some instances, all three sets of coils of the gradient coils 202 may be energized and three gradient fields may be generated thereby. In some embodiments of the present disclosure, the X coils and Y coils may be energized to generate the gradient fields in the X direction and the Y direction. As used herein, the X axis, the Y axis, the Z axis, the X direction, the Y direction, and the Z direction in the description of FIG. 2 are the same as or similar to those described in FIG. 1.

In some embodiments, radio frequency (RF) coils 203 may be located inside the main magnet 201 and serve as transmitters, receivers, or both. The RF coils 203 may be in connection with RF electronics 209 that may be configured or used as one or more integrated circuits (ICs) functioning as a waveform transmitter and/or a waveform receiver. The RF electronics 209 may be connected to a radiofrequency power amplifier (RFPA) 207 and an analog-to-digital converter (ADC) 208.

When used as transmitters, the RF coils 203 may generate RF signals that provide a third magnetic field that is utilized to generate MR signals related to the object being imaged. The third magnetic field may be perpendicular to the main magnetic field. The waveform generator 216 may generate an RF pulse. The RF pulse may be amplified by the RFPA 207, processed by the RF electronics 209, and applied to the RF coils 203 to generate the RF signals in response to a powerful current generated by the RF electronics 209 based on the amplified RF pulse.

When used as receivers, the RF coils may be responsible for detecting MR signals (e.g., echoes). After excitation, the MR signals generated by the object may be sensed by the RF coils 203. The receive amplifier then may receive the sensed MR signals from the RF coils 203, amplify the sensed MR signals, and provide the amplified MR signals to the ADC 208. The ADC 208 may transform the MR signals from analog signals to digital signals. The digital MR signals then may be filled into k-space.

In some embodiments, the gradient coils 202 and the RF coils 203 may be circumferentially positioned with respect to the object. It is understood by those skilled in the art that the main magnet 201, the gradient coils 202, and the RF coils 203 may be situated in a variety of configurations around the object.

In some embodiments, the RFPA 207 may amplify an RF pulse (e.g., the power of the RF pulse, the voltage of the RF pulse) such that an amplified RF pulse is generated to drive the RF coils 203. The RFPA 207 may include a transistor-based RFPA, a vacuum tube-based RFPA, or the like, or any combination thereof. The transistor-based RFPA may include one or more transistors. The vacuum tube-based RFPA may include a triode, a tetrode, a klystron, or the like, or any combination thereof. In some embodiments, the RFPA 207 may include a linear RFPA, or a nonlinear RFPA. In some embodiments, the RFPA 207 may include one or more RFPAs.

In some embodiments, the scanner 110 may further include an object positioning system (not shown). The object positioning system may include an object cradle and a transport device. The object may be placed on the object cradle and be positioned by the transport device within the bore of the main magnet 201.

MRI systems (e.g., the MRI system 100 in the present disclosure) may be commonly used to obtain an interior image from an object (e.g., a patient) for a particular region of interest that can be used for the purposes of, e.g., diagnosis, treatment, or the like, or a combination thereof. MRI systems include a main magnet (e.g., the main magnet 201) assembly for providing a main magnetic field to align the individual magnetic moments of the H atoms within the patient's body. During this process, the H atoms oscillate around their magnetic poles at their characteristic Larmor frequency. If the object is subjected to an additional magnetic field, which is tuned to the Larmor frequency, the H atoms absorb additional energy, which rotates the net aligned moment of the H atoms. The additional magnetic field may be provided by an RF excitation signal (e.g., the RF signal generated by the RF coils 203). When the additional magnetic field is removed, the magnetic moments of the H atoms rotate back into alignment with the main magnetic field, thereby emitting an MR signal. The MR signal is received and processed to form an MR image. T1 relaxation may be the process by which the net magnetization grows/returns to its initial maximum value parallel to the main magnetic field. T1 may be the time constant for regrowth of longitudinal magnetization (e.g., along the main magnetic field). T2 relaxation may be the process by which the transverse components of magnetization decay or dephase. T2 may be the time constant for decay/dephasing of transverse magnetization. In the present disclosure, terms "MR data," "MR signal," "echo," "echo data," and "echo signal" may be used interchangeably.

If the main magnetic field is uniform across the entire body of the patient, then the RF excitation signal may excite all of the H atoms in the sample non-selectively. Accordingly, in order to image a particular portion of the patient's body, magnetic field gradients Gx, Gy, and Gz (e.g., generated by the gradient coils 202) in the X, Y, and Z directions (e.g., same as or similar to the X axis, the Y axis, and the Z axis in FIG. 1), having a particular timing, frequency, and phase, may be superimposed on the magnetic field such that the RF excitation signal excites the H atoms in one or more target slices of the patient's body, and unique phase and frequency information is encoded in the MR signal depending on the location of the H atoms in the "image slice."

Typically, portions of the patient's body to be imaged are scanned by a sequence of measurement cycles in which the RF excitation signals and the magnetic field gradients Gx, Gy and Gz vary according to an MRI imaging protocol that is being used. A protocol may be designed for one or more tissues to be imaged, diseases, and/or clinical scenarios. A protocol may include a certain number of pulse sequences oriented in different planes and/or with different parameters. The pulse sequences may include spin echo sequences, gradient echo sequences, diffusion sequences, inversion recovery sequences, saturation recovery sequences, or the like, or any combination thereof. For instance, the spin echo sequences may include fast spin echo (FSE), turbo spin echo (TSE), rapid acquisition with relaxation enhancement (RARE), half-Fourier acquisition single-shot turbo spin-echo (HASTE), turbo gradient spin echo (TGSE), or the like, or any combination thereof. The protocol may also include information regarding image contrast and/or ratio, a region of interest (ROI), slice thickness, an imaging type (e.g., T1 weighted imaging, T2 weighted imaging, proton density weighted imaging, etc.), T1, T2, an echo type (spin echo, fast spin echo (FSE), fast recovery FSE, single shot FSE, gradient recalled echo, fast imaging with stead-state procession, and so on), a flip angle value, acquisition time (TA), echo time (TE), repetition time (TR), echo train length (ETL), the number of phases, the number of excitations (NEX), inversion time, bandwidth (e.g., RF receiver bandwidth, RF transmitter bandwidth, etc.), one or more image reconstruction algorithms, or the like, or any combination thereof.

For an MRI scan, the acquired MR signals (also referred to as MR data) may be digitized and filled into the k-space. One or more images may be generated based on the MR data in accordance with the MRI imaging protocol that is used.

FIG. 3 is a schematic diagram illustrating exemplary hardware and/or software components of a computing device on which the processing device 140 may be implemented according to some embodiments of the present disclosure. As illustrated in FIG. 3, the computing device 300 may include a processor 310, a storage 320, an input/output (I/O) 330, and a communication port 340.

The processor 310 may execute computer instructions (program code) and perform functions of the processing device 140 in accordance with techniques described herein. The computer instructions may include routines, programs, objects, components, signals, data structures, procedures, modules, and functions, which perform particular functions described herein. For example, the processor 310 may generate one or more images based on MR data. In some embodiments, the processor 310 may include a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration purposes, only one processor is described in the computing device 300. However, it should be noted that the computing device 300 in the present disclosure may also include multiple processors, and thus operations of a method that are performed by one processor as described in the present disclosure may also be jointly or separately performed by the multiple processors. For example, if in the present disclosure the processor of the computing device 300 executes both operations A and B, it should be understood that operations A and B may also be performed by two different processors jointly or separately in the computing device 300 (e.g., a first processor executes operation A and a second processor executes operation B, or the first and second processors jointly execute operations A and B).

Merely by way example, the processor 310 may receive instructions to follow an MRI scan protocol for imaging/scanning the object. For example, the processor 310 may instruct the object positioning system of the scanner 110 to move the object to a proper position within the bore of the main magnet 201. As another example, the processor 310 may also provide certain control signals to control the main magnet 201 to generate a main magnet field with a specific strength.

The processor 310 may receive control signals to set the shape, amplitude, and/or timing of the gradient waveforms and/or the RF waveforms, and send the set parameters to the waveform generator 216 to instruct the waveform generator 216 to generate a particular gradient waveform sequence and pulse sequence that are to be applied to the gradient coils 202 and the RF coils 203 through the amplifiers 204-207, respectively.

The processor 310 may also sample data (e.g., echoes) from the RF coils 203 based on one or more sampling parameters including, e.g., timing information (e.g., the length of data acquisition), the type of k-space data acquisition (e.g., undersampling, oversampling, etc.), sampling trajectory (e.g., a Cartesian trajectory, a non-Cartesian trajectory such as spiral trajectory, radial trajectory, etc.), or the like, or a combination thereof. In some embodiments, the timing information may be input by a user (e.g., an operator) or autonomously determined by the MRI system 100 based on one or more other parameters (e.g., clinical needs) of an imaging process. The timing information may correspond to the type of the gradient and RF waveforms that are sent to the gradient coils 202 and the RF coils 203, respectively, so that the MR signals are correctly sampled. The processor 310 may also generate one or more MR images by reconstructing the sampled MR data.

The storage 320 may store data/information obtained from the scanner 110, the user device 130, the storage device 150, or any other component of the MRI system 100. In some embodiments, the storage 320 may include a mass storage device, a removable storage device, a volatile read-and-write memory, a read-only memory (ROM), or the like, or any combination thereof. For example, the mass storage device may include a magnetic disk, an optical disk, a solid-state drive, etc. The removable storage device may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage 320 may store one or more programs and/or instructions to perform exemplary methods described in the present disclosure. For example, the storage 320 may store a program for the processing device 140 for generating one or more images based on MR data. In some embodiments, the storage 320 may store one or more reconstructed MRI images.

The I/O 330 may input or output signals, data, or information. In some embodiments, the I/O 330 may enable user interaction with the processing device 140. In some embodiments, the I/O 330 may include an input device and an output device. Exemplary input devices may include a keyboard, a mouse, a touch screen, a microphone, a trackball, or the like, or a combination thereof. Exemplary output devices may include a display device, a loudspeaker, a printer, a projector, or the like, or a combination thereof. Exemplary display devices may include a liquid crystal display (LCD), a light-emitting diode (LED)-based display, a flat panel display, a curved screen, a television device, a cathode ray tube (CRT), or the like, or a combination thereof.

The communication port 340 may be connected to a network (e.g., the network 120) to facilitate data communications. The communication port 340 may establish connections between the processing device 140 and the scanner 110, the user device 130, or the storage device 150. The connection may be a wired connection, a wireless connection, or a combination of both that enables data transmission and reception. The wired connection may include an electrical cable, an optical cable, a telephone wire, or the like, or any combination thereof. The wireless connection may include Bluetooth, Wi-Fi, WiMax, WLAN, ZigBee, mobile network (e.g., 3G, 4G, 5G, etc.), or the like, or a combination thereof. In some embodiments, the communication port 340 may be a standardized communication port, such as RS232, RS485, etc. In some embodiments, the communication port 340 may be a specially designed communication port. For example, the communication port 340 may be designed in accordance with the digital imaging and communications in medicine (DICOM) protocol.

Figure 4:
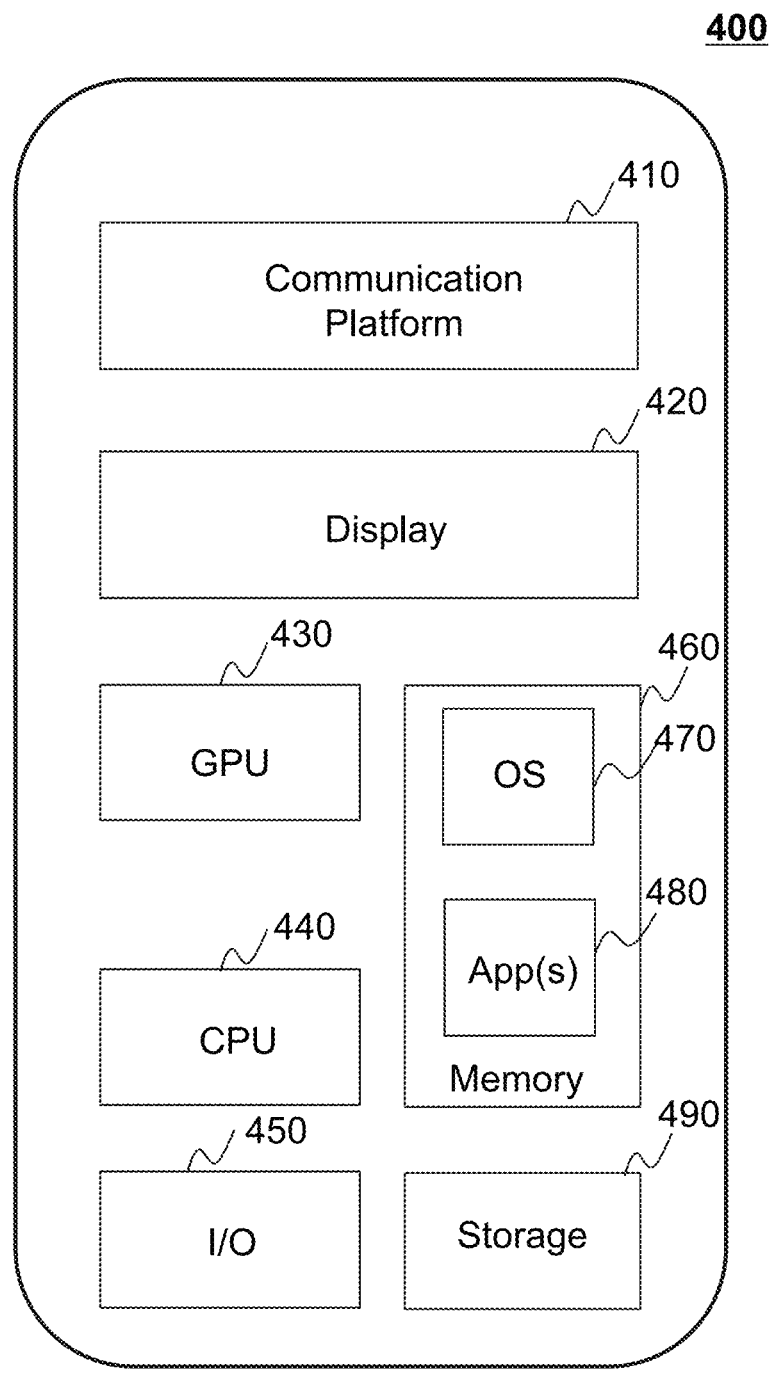
FIG. 4 is a schematic diagram illustrating exemplary hardware and/or software components of a mobile device according to some embodiments of the present disclosure.

FIG. 4 is a schematic diagram illustrating exemplary hardware and/or software components of a mobile device on which the user device 130 may be implemented according to some embodiments of the present disclosure. As illustrated in FIG. 4, the mobile device 400 may include a communication platform 410, a display 420, a graphics processing unit (GPU) 430, a central processing unit (CPU) 440, an I/O 450, a memory 460, and a storage 490. In some embodiments, any other suitable component, including but not limited to a system bus or a controller (not shown), may also be included in the mobile device 400. In some embodiments, a mobile operating system 470 (e.g., iOS, Android, Windows Phone, etc.) and one or more applications 480 may be loaded into the memory 460 from the storage 490 in order to be executed by the CPU 440. The applications 480 may include a browser or any other suitable mobile apps for receiving and rendering information relating to image processing or other information from the processing device 140. User interactions with the information stream may be achieved via the I/O 450 and provided to the processing device 140 and/or other components of the MRI system 100 via the network 120. Merely by way of example, a user (e.g., a doctor, a technician, an engineer, an operator, etc.) of the MRI system 100 may input data related to an object (e.g., a patient) that is being/to be imaged/scanned through the I/O 450. The data related to the object may include identification information (e.g., the name, age, gender, medical history, contact information, physical examination result, etc.) and/or the test information including the nature of the MRI scan that needs to be performed. The user may also input parameters needed for the operation of the scanner 110, such as image contrast and/or ratio, a region of interest (ROI), slice thickness, an imaging type (e.g., T1 weighted imaging, T2 weighted imaging, proton density weighted imaging, etc.), T1, T2, an echo type (spin echo, fast spin echo (FSE), fast recovery FSE, single shot FSE, gradient recalled echo, fast imaging with steady-state procession, and so on), a flip angle value, acquisition time (TA), echo time (TE), repetition time (TR), inversion time (TI), saturation time (TS), echo train length (ETL), the number of phases, the number of excitations (NEX), bandwidth (e.g., RF receiver bandwidth, RF transmitter bandwidth, etc.), a scan type, a type of sampling, time points when the MR data is acquired (e.g., cardiac phases, respiratory phases, etc.), time points when an acquisition phase of the scan is triggered, a duration of a period of the acquisition phase, or the like, or any combination thereof. The I/O may also display MR images generated based on the sampled data.

In some embodiments, the I/O 450 may include an input device and an output device. Exemplary input devices may include a keyboard, a mouse, a touch screen, a microphone, a trackball, or the like, or a combination thereof. Exemplary output devices may include a display device, a loudspeaker, a printer, a projector, or the like, or a combination thereof. Exemplary display devices may include a liquid crystal display (LCD), a light-emitting diode (LED)-based display, a flat panel display, a curved screen, a television device, a cathode ray tube (CRT), or the like, or a combination thereof.

To implement various modules, units, and their functionalities described in the present disclosure, computer hardware platforms may be used as the hardware platform(s) for one or more of the elements described herein. The hardware elements, operating systems and programming languages of such computers are conventional in nature, and it is presumed that those skilled in the art are adequately familiar therewith to adapt those technologies to the blood pressure monitoring as described herein. A computer with user interface elements may be used to implement a personal computer (PC) or another type of work station or terminal device, although a computer may also act as a server if appropriately programmed. It is believed that those skilled in the art are familiar with the structure, programming and general operation of such computer equipment and as a result the drawings should be self-explanatory.

Figure 5:
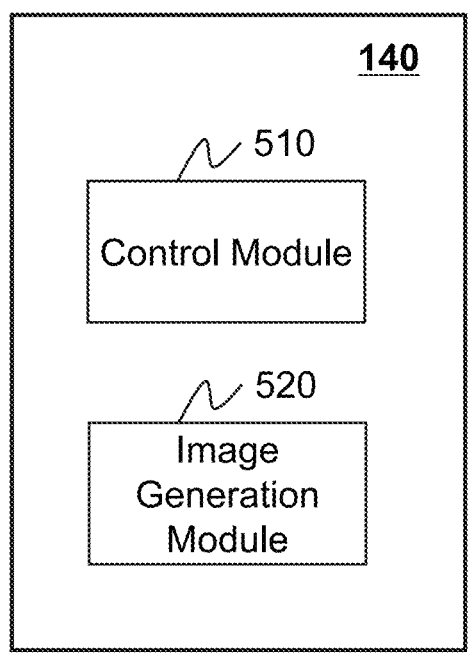
FIG. 5 is a schematic block diagram illustrating an exemplary processing device according to some embodiments of the present disclosure.

FIG. 5 is a schematic block diagram illustrating an exemplary processing device according to some embodiments of the present disclosure. The processing device 140 may include a control module 510 and an image generation module 520.

The control module 510 may cause, based on a pulse sequence, a magnetic resonance (MR) scanner (e.g., the scanner 110) to perform a scan on an object. In some embodiments, a process of the scan may include a plurality of repetition times (TRs). A TR may be between centers of two consecutive excitation RF pulses applied in the scan. In some embodiments, the pulse sequence may include a steady-state sequence and an acquisition sequence. In some embodiments, the acquisition sequence or the steady-state sequence may correspond to or include one of the plurality of TRs. In the present disclosure, the terms "excitation pulse," "RF excitation signal," and "excitation RF pulse" are used interchangeably.

In some embodiments, a process of the scan may include a steady-state phase. No MR data may be acquired by the scanner 110 in the steady-state phase. The process of the scan may include an acquisition phase in which MR data of the object is acquired by the scanner 110. In the steady-state phase of the scan, the control module 510 may cause the scanner 110 to operate based on the steady sequence. In an acquisition phase of the scan, the control module 510 may cause the scanner 110 to operate based on the acquisition sequence. In some embodiments, the steady-state phase may include a first count (e.g., greater than or equal to 1) of the plurality of TRs in each of which the control module 510 may cause the scanner 110 to operate based on the steady sequence. The acquisition phase may include a second count (e.g., greater than or equal to 1) of the plurality of TRs in each of which the control module 510 may cause the scanner 110 to operate based on the acquisition sequence. In some embodiments, the first count may be the same as or different from the second count.

In some embodiments, the control module 510 may cause the scanner 110 to perform the scan during one or more cycles of a physiological motion of the object. The physiological motion of the object may include respiratory motion, cardiac motion, etc. The one or more cycles of the physiological motion of the object in the scan may include the steady-state phase and the acquisition phase.

In some embodiments, the steady-state phase may include one or more steady-state sub-phases each of which corresponds to one of the one or more cycles of the physiological motion. The acquisition phase may include one or more acquisition sub-phases each of which corresponds to one of the one or more cycles of the physiological motion. One of the one or more cycles of the physiological motion may include a corresponding acquisition sub-phase and a corresponding steady-state sub-phase.

In some embodiments, acquisition sub-phases and corresponding steady-state phases may be periodically distributed in two or more cycles. For example, a length of time or duration of each of the acquisition sub-phases may be the same. An interval between two consecutive acquisition sub-phases corresponding to each pair of consecutive cycles of the two or more cycles may be the same. A length of time or duration of each of the steady-state sub-phases may be the same. An interval between two consecutive steady-state sub-phases corresponding to each pair of two consecutive cycles of the two or more cycles may be the same.

In some embodiments, the processing device 140 may determine whether to trigger the acquisition phase of the scan using a gating technique, such as respiration gating, electrocardiogram (ECG) gating, pulse gating, etc.

In some embodiments, the control module 510 may obtain a physiological signal of the object during the scan. The physiological signal may include a respiration signal, an ECG signal, and a pulse signal, etc. In some embodiments, a physiological signal acquisition device may acquire the physiological signal of the object. The control module 510 may obtain the physiological signal from the physiological signal acquisition device.

In some embodiments, an amplitude of the physiological signal may indicate a motion phase of the physiological motion. For example, the amplitude of the respiration signal may represent pressures of the lungs of the object at different times of the scan, volumes of the lungs of the object at different times of the scan, expiratory volumes at different times of the scan, or inspiratory volumes at different times of the scan, etc., which may indicate a respiration phase of the respiratory motion, such as an expiration phase and an inspiration phase. As another example, the amplitude of the ECG signal and/or the pulse signal may represent a voltage of the ECG signal and/or the pulse signal, which may indicate a cardiac phase of the cardiac motion, such as diastole and systole.

Merely by way of example, a trigger process for determining whether to trigger the acquisition phase in a cycle of the physiological motion may be described below. In some embodiments, the trigger process may be applied to at least one of the one or more cycles of the physiological motion.

In some embodiments, the control module 510 may determine whether the acquisition phase needs to be triggered in the cycle (e.g., whether the acquisition sub-phase of the acquisition phase corresponding to the cycle needs to be triggered) based on the physiological signal. In response to determining that the corresponding acquisition sub-phase does not need to be triggered, the control module 510 may cause the scanner 110 to operate based on the steady-state sequence. In response to determining that the corresponding acquisition sub-phase needs to be triggered, the control module 510 may cause the scanner 110 to operate based on the acquisition sequence.

In some embodiments, the control module 510 may set a trigger condition. When detecting that at least one portion of the physiological signal satisfies the trigger condition, the control module 510 may initiate an acquisition sub-phase immediately or after a period of time (also referred to as a delay time, abbreviated to TD). In some embodiments, in a cycle, the time outside the acquisition sub-phase may be deemed the corresponding steady-state sub-phase. As used herein, "immediately" suggests that an acquisition sub-phase is initiated within a short period of time, e.g., less than 30 seconds, or 20 seconds, or 10 seconds, or 5 seconds, or 1 second, from the detection that at least one portion of the physiological signal satisfies the trigger condition. In some embodiments, the TD may be 5 seconds, 10 seconds, 30 seconds, 1 minute, more, from the detection that at least one portion of the physiological signal satisfies the trigger condition. In a cycle, the at least one portion of the physiological signal that satisfies the trigger condition may be referred to as a reference portion or a trigger portion.

In some embodiments, the trigger condition may relate to an amplitude and/or an acquisition time of the reference portion, when the reference portion is detected within a cycle of a physiological motion, etc. For instance, the trigger condition may include that an amplitude of the reference portion is within an amplitude range, the reference portion is acquired within a time range of the cycle of the physiological motion, or the like, or any combination thereof. For example, if the acquired physiological signal is the ECG signal, the reference portion may be one portion of the ECG signal that represents an R wave of the ECG signal in the cycle.

In some embodiments, the acquisition sequence and the steady sequence may include pulse information of at least one pulse, such as an RF pulse (e.g., an excitation RF pulse), and/or a magnetic field gradient (e.g., a slice selection gradient, a readout gradient, a phase encoding gradient, a dephasing gradient, etc.). Pulse information of a pulse may include a waveform of the pulse, timing information (e.g., indicating the time to start to impose the pulse) of the pulse, a flip angle of the pulse, a direction along which the pulse is imposed, or the like, or any combination thereof. In some embodiments, the acquisition sequence and the steady sequence may be different in applying one or more magnetic field gradients. The one or more magnetic field gradients may include a slice selection gradient, a readout gradient, a phase encoding gradient, a dephasing gradient, or the like, or any combination thereof.

In some embodiments, the acquisition sequence may include a first excitation RF pulse with a flip angle. The first excitation RF pulse may be configured to tip a portion of the longitudinal magnetization of the object into the transverse plane. The flip angle may refer to the rotation of the net magnetization vector by an RF pulse (e.g., the first excitation RF pulse) relative to the main magnetic field. In some embodiments, the flip angle of the first excitation RF pulse may be any value. For example, the flip angle of the first excitation RF pulse may be equal to or less than 90°.

In some embodiments, the acquisition sequence may include a first slice selection gradient. The first slice selection gradient may be imposed along a first direction perpendicular to a plane of one or more target slices of the object, resulting in a linear variation of potential resonance frequencies in the first direction. For example, if the plane of the one or more target slices of the object is parallel to the plane XY in FIG. 1, the first slice selection gradient may be imposed along the Z direction in FIG. 1. The first excitation RF pulse may be a tailored RF pulse, of which the frequency components may match the range of frequencies included in the one or more target slices. The first slice selection gradient and the first excitation RF pulse may be combined such that the one or more target slices are excited. In some embodiments, the stronger the field intensity of the first slice selection gradient is, the smaller the thickness of the one or more target slices may be.

In some embodiment, the acquisition sequence may include one or more readout gradients (also referred to as frequency encoding gradients) and one or more phase encoding gradients. In some embodiments, the one or more readout gradients may be imposed along a second direction. The one or more phase encoding gradients may be imposed along a third direction. The one or more target slices may include a plurality of voxels of the object. The one or more readout gradients and the one or more phase encoding gradients may spatially encode at least a portion of the plurality of voxels along the second direction and the third direction. In some embodiments, the first direction, the second direction, and the third direction may be perpendicular to each other. For example, if the plane of the one or more target slices of the object is parallel to the plane XY in FIG. 1, the second direction may be the X direction in FIG. 1, and the third direction may be the Y direction in FIG. 1, or the second direction may be the Y direction in FIG. 1, and the third direction may be the X direction in FIG. 1.

After the first excitation RF pulse, under the influence of at least one of the first slice selection gradient, the one or more readout gradients, and the one or more phase encoding gradients, the procession of the protons in the object may be dephased because the main magnetic field is non-uniform. Dephasing of the procession of the protons in the object may affect the phase encoding of the one or more target slices. In some embodiments, the acquisition sequence may include one or more first dephasing gradients configured to reduce or remove the dephasing of the procession of the protons caused by the non-uniformity of the main magnetic field. In some embodiments, the one or more first dephasing gradients may be imposed along at least one of the first direction, the second direction, and the third direction.

In some embodiments, when the control module 510 causes the scanner 110 to operate based on the acquisition sequence in one TR of the acquisition phase of the scan, the RF coils 203 may output the first excitation RF pulse. If the plane of one or more target slices of the object is parallel to the XY plane in FIG. 1, the Z coils of the gradient coils 202 (as illustrated in FIG. 2) may output the first slice selection gradient. The X coils (or the Y coils) of the gradient coils 202 (as illustrated in FIG. 2) may output the one or more readout gradients, and the Y coils (or the X coils) of the gradient coils 202 (as illustrated in FIG. 2) may output the one or more phase encoding gradients. At least one of the X coils, the Y coils, and the Z coils of the gradient coils 202 may output the one or more first dephasing gradients. According to the acquisition sequence, one or more echoes may be generated in the TR. The one or more echoes may be received by the RF coils 203. The ADC 208 may convert the one or more acquired echoes to digitized data.

In some embodiments, the steady-state sequence may include a second excitation RF pulse that is the same as the first excitation RF pulse, a second slice selection gradient that is the same as the first slice selection gradient, and one or more second dephasing gradients that are configured to reduce or remove the dephasing of the procession of the protons caused by the non-uniformity of the main magnetic field. In some embodiments, the one or more second dephasing gradients may be imposed along the one or more directions (also referred to as dephasing direction) along which the one or more first dephasing gradients are imposed. For example, the one or more first dephasing gradients and the one or more second dephasing gradients may be imposed along the second direction of the readout gradient. In some embodiments, a count of the one or more second dephasing gradients may be equal to or different from a count of the one or more first dephasing gradients.

In some embodiments, the steady-state sequence may be free of any readout gradient and/or any phase encoding gradient. In some embodiments, waveforms of at least one of the one or more second dephasing gradients and at least one of the one or more first dephasing gradients that are imposed along the same dephasing direction may be the same or different.

In some embodiments, in order to make the effect of reducing or removing the dephasing of the one or more first dephasing gradients and the one or more second dephasing gradients consistent, a zeroth moment of the one or more first dephasing gradients may be equal to a zeroth moment of the one or more second dephasing gradients, a zeroth moment of a gradient (e.g., the first dephasing gradient or the second dephasing gradient) may refer to an area under a waveform of the gradient. In some embodiments, the zeroth moment of at least one of the one or more second dephasing gradients and the zeroth moment of at least one of the one or more first dephasing gradients that are imposed along the same dephasing direction may be the same.

In some embodiments, the loudness of noise caused by a gradient (e.g., the readout gradient, the phase encoding gradient, the first dephasing gradient, and the second dephasing gradient) may depend on an effective amplitude and a slew rate of the gradient. The greater the effective amplitude and/or the slew rate of the gradient is, the greater the Lorentz force caused by the gradient may be, and the louder or higher the noise caused by the gradient may be. The effective amplitude may be kept for a period of time (also referred to as an effective amplitude time) in the gradient to realize the function of the gradient (e.g., spatially encoding the one or more target slices of the object, or reducing or removing the dephasing). In some embodiments, the effective amplitude of the gradient may refer to the maximum amplitude of the gradient. The slew rate of the gradient may refer to a ratio of the effective amplitude of the gradient to a climb time of the gradient. The climb time of the gradient may refer to a time period in which the amplitude of the gradient changes from 0 to the effective amplitude.

In some embodiments, a duration of a first dephasing period of the first dephasing gradient may be shorter than a duration of a second dephasing period of the second dephasing gradient. In some embodiments, an effective amplitude of the second dephasing gradient may be smaller than an effective amplitude of the first dephasing gradient. In some embodiments, a slew rate of the second dephasing gradient is lower than a slew rate of the first dephasing gradient.

In some embodiments, when the control module 510 causes the scanner 110 to operate based on the steady sequence in one TR of the steady-state phase of the scan, the RF coils 203 may output the second excitation RF pulse. If the plane of one or more target slices of the object is parallel to the XY plane in FIG. 1, the Z coils of the gradient coils 202 (as illustrated in FIG. 2) may output the second slice selection gradient. The X coils and the Y coils of the gradient coils 202 (as illustrated in FIG. 2) may not output any phase encoding gradient and/or any readout gradient. At least one of the X coils, the Y coils, and the Z coils of the gradient coils 202 may output the one or more second dephasing gradients.

In some embodiments, the existence of the excitation RF pulse, the slice selection gradient, and the second dephasing gradient in the steady sequence may make the precession of the protons of the object stable when the scanner 110 operates based on the steady sequence. Compared to the acquisition sequence, when the scanner 110 operates based on the steady sequence, the absence of any phase encoding gradient and/or any readout gradient in the steady sequence may make the scanner 110 generate less noise. Compared to the first dephasing gradient of the acquisition sequence, the second dephasing gradient with the smaller effective amplitude and/or the lower slew rate may further make the scanner 110 generate less noise.

In some embodiments, in the steady-state phase of the scan, the control module 510 may also cause the scanner 110 to operate based on the acquisition sequence. However, in the steady-state phase of the scan, compared to operating based on the acquisition sequence, when the scanner 110 operates based on the steady sequence according to some embodiments described in the present disclosure, the sound the scanner 110 generates during the scan may be of less loudness and a stronger rhythm, which may make the physiological motion of the object more smooth or stable (e.g., making the object breathe more smoothly), thereby improving the accuracy of the triggering of the acquisition phase based on the physiological signal of the physiological motion and/or reducing motion artifacts in one or more images.

In some embodiments, the acquired MR data may be filled into the k-space based on the pulse sequence. In some embodiments, the acquired MR data may be filled into the k-space based on the acquisition sequence of the pulse sequence. In some embodiments, a plurality of echoes may be acquired in the scan. The ADC 208 may convert the plurality of acquired echoes from analog signals to digitized data (e.g., digitized echoes). The digitized echoes may be filled into the k-space.

In some embodiments, according to the one or more readout gradients and the one or more phase encoding gradients applied in the acquisition phase of the scan, phase information and frequency information may be encoded in the acquired echoes. The digitized echoes may be filled into the k-space based on the phase information and the frequency information.

In some embodiments, the Kx axis of the k-space (e.g., as shown in FIG. 10A and FIG. 10B) may represent phase encoding of the MR data, and the Ky axis of the k-space (e.g., as shown in FIG. 10A and FIG. 10B) may represent frequency encoding of the MR data. A manner in which the plurality of echoes is sampled to be filled into the k-space may be referred to as a k-space trajectory. The k-space trajectory may include a Cartesian trajectory and a non-Cartesian trajectory. In the Cartesian trajectory, each of the digitized echoes may fill a line of the k-space along the Kx direction of the k-space. The line of the k-space may be along the Ky direction of the k-space. The non-Cartesian trajectory may include a spiral trajectory, a radial trajectory, a zig-zag trajectory, etc.

In some embodiments, as used in the present disclosure, data in the k-space corresponding to an echo may be referred to as a data line. In some embodiments, the plurality of echoes may be filled into the k-space in a linear manner or a segmented manner. In the linear manner, the data lines corresponding to the plurality of echoes may be distributed in the k-space in an order in which the plurality of echoes are acquired.

In some embodiments, when the scan is performed during two or more cycles of the physiological motion of the object, the plurality of echoes may be filled into the k-space based on a segmented manner. In the segmented manner, the k-space may be divided into a plurality of regions based on a count of echoes acquired in each of the two or more cycles. For example, if 4 echoes are acquired in each of the two or more cycles, the k-space may be divided into 4 regions. The echoes acquired in different cycles of the two or more cycles may be filled in same regions of the plurality of regions. The echoes acquired in a same cycle of the two or more cycles may be filled in different regions of the plurality of regions. In some embodiments, each of the plurality of echoes acquired in each of the two or more cycles may correspond to a motion phase of the physiological motion of the object. The motion phase corresponding to an echo may indicate a motion state of the physiological motion of the object during the acquisition time of the echo. The echoes corresponding to a same motion phase may be filled into a same region of the plurality of regions.

Merely by way of example, the scan may be performed during two or more cycles of the physiological motion of the object, and n echoes may be acquired and filled into the k-space based on the Cartesian trajectory. In each of the two or more cycles of the physiological motion, 4 of the n echoes may be acquired.

In some embodiments, if the physiological signal are used to trigger the acquisition phase of the scan, each of the 4 echoes acquired in each cycle may correspond to a portion of a curve of the physiological signal. The portion of the curve of the physiological signal may represent a motion phase of the physiological motion during the acquisition time of the echo. The data line corresponding to the echo may also correspond to the portion of the curve of the physiological signal. A sequence, along a certain direction (e.g., the Kx direction of the k-space), of the motion phases (or the corresponding portions of the curve of the physiological signal) of the data lines in the k-space may be referred to as a motion modulation form of the k-space.

In some embodiments, the segmented manner may also be applied in a scan that is performed during one or more cycles of the physiological motion of the object and without the steady-state phase.

The image generation module 520 may generate one or more images of the object based on the MR data.

The modules in the processing device 140 may be connected to or communicate with each other via a wired connection or a wireless connection. The wired connection may include a metal cable, an optical cable, a hybrid cable, or the like, or any combination thereof. The wireless connection may include a Local Area Network (LAN), a Wide Area Network (WAN), a Bluetooth, a ZigBee, a Near Field Communication (NFC), or the like, or any combination thereof. Two or more of the modules may be combined as a single module, and any one of the modules may be divided into two or more units.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the processing device 140 may further include a storage module (not shown in FIG. 5). The storage module may be configured to store data generated during any process performed by any component of the processing device 140. As another example, each of the components of the processing device 140 may include a storage device. Additionally or alternatively, the components of the processing device 140 may share a common storage device.

Figure 6A:
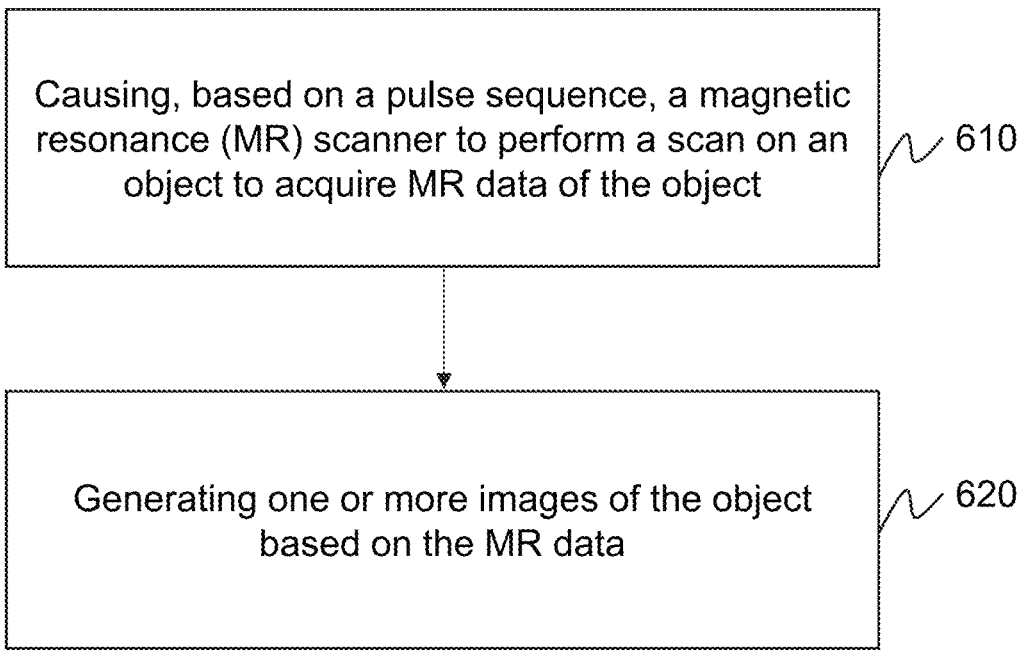
FIG. 6A is a flowchart illustrating an exemplary process for MRI according to some embodiments of the present disclosure.

FIG. 6A is a flowchart illustrating an exemplary process for MRI according to some embodiments of the present disclosure. In some embodiments, the process 600 may be implemented in the MRI system 100 illustrated in FIG. 1. For example, the process 600 may be stored in a storage device (e.g., the storage device 150, or the storage 320 of the processing device 140) as a form of instructions, and can be invoked and/or executed by the processing device 140 (e.g., the processor 310 of the processing device 140, or one or more modules in the processing device 140 illustrated in FIG. 5). The operations of the illustrated process 600 presented below are intended to be illustrative. In some embodiments, the process 600 may be accomplished with one or more additional operations not described, and/or without one or more of the operations discussed. Additionally, the order in which the operations of the process 600 as illustrated in FIG. 6A and described below is not intended to be limiting.

In 610, the processing device 140 (e.g., the control module 510) may cause, based on a pulse sequence, a magnetic resonance (MR) scanner (e.g., the scanner 110) to perform a scan on an object. In some embodiments, a process of the scan may include a plurality of repetition times (TRs). A TR may be between centers of two consecutive excitation RF pulses applied in the scan. In some embodiments, the pulse sequence may include a steady-state sequence and an acquisition sequence. In some embodiments, the acquisition sequence or the steady-state sequence may correspond to or include one of the plurality of TRs. In the present disclosure, the terms "excitation pulse," "RF excitation signal," and "excitation RF pulse" are used interchangeably.

In some embodiments, a process of the scan may include a steady-state phase and an acquisition phase. In some embodiments, no MR data may be acquired by the scanner 110 in the steady-state phase. In some embodiments, MR data acquired by the scanner 110 in the steady-state phase may not be used to generate an MR image (e.g., may not be filled into k-space). In some embodiments, MR data acquired by the scanner 110 in the acquisition phase may be used to generate an MR image.

In the steady-state phase of the scan, the processing device 140 may cause the scanner 110 to operate based on the steady sequence. In an acquisition phase of the scan, the processing device 140 may cause the scanner 110 to operate based on the acquisition sequence. In some embodiments, the steady-state phase may include a first count (e.g., greater than or equal to 1) of the plurality of TRs in each of which the processing device 140 may cause the scanner 110 to operate based on the steady sequence. The acquisition phase may include a second count (e.g., greater than or equal to 1) of the plurality of TRs in each of which the processing device 140 may cause the scanner 110 to operate based on the acquisition sequence. In some embodiments, the first count may be the same as or different from the second count.

In some embodiments, the processing device 140 may cause the scanner 110 to perform the scan during one or more cycles of a physiological motion of the object. The physiological motion of the object may include respiratory motion, cardiac motion, etc. The one or more cycles of the physiological motion of the object in the scan may include the steady-state phase and the acquisition phase.

In some embodiments, the steady-state phase may include one or more steady-state sub-phases each of which corresponds to one of the one or more cycles of the physiological motion. The acquisition phase may include one or more acquisition sub-phases each of which corresponds to one of the one or more cycles of the physiological motion. One of the one or more cycles of the physiological motion may include a corresponding acquisition sub-phase and a corresponding steady-state sub-phase.

In some embodiments, acquisition sub-phases and corresponding steady-state phases may be periodically distributed in two or more cycles. For example, a length of time or duration of each of the acquisition sub-phases may be the same. An interval between two consecutive acquisition sub-phases corresponding to each pair of consecutive cycles of the two or more cycles may be the same. A length of time or duration of each of the steady-state sub-phases may be the same. An interval between two consecutive steady-state sub-phases corresponding to each pair of two consecutive cycles of the two or more cycles may be the same.

Figure 6B:
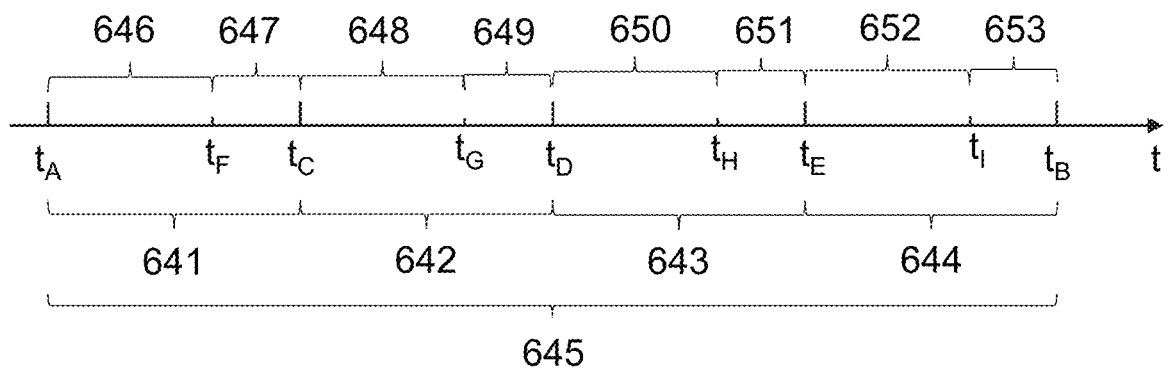
FIG. 6B is a schematic diagram illustrating exemplary cycles of a physiological motion of an object included in a scan of the object according to some embodiments of the present disclosure.

FIG. 6B is a schematic diagram illustrating exemplary cycles of a physiological motion of the object included in a scan of the object according to some embodiments of the present disclosure. As shown in FIG. 6B, a scan 645 may be performed on an object during $t_A$-$t_B$. The scan 645 may include 4 cycles of a physiological motion of the object, such as cycle 641 from $t_A$-$t_C$, cycle 642 from $t_C$-$t_D$, cycle 643 from $t_D$-$t_E$, and cycle 644 from $t_E$-$t_B$. Period 646 from $t_A$-$t_F$ may refer to a steady-state sub-phase corresponding to the cycle 641. Period 647 from $t_F$-$t_C$ may refer to an acquisition sub-phase corresponding to the cycle 641. Period 648 from $t_C$-$t_G$ may refer to a steady-state sub-phase corresponding to the cycle 642. Period 649 from $t_G$-$t_D$ may refer to an acquisition sub-phase corresponding to the cycle 642. Period 650 from $t_D$-$t_H$ may refer to a steady-state sub-phase corresponding to the cycle 643. Period 651 from $t_H$-$t_E$ may refer to an acquisition sub-phase corresponding to the cycle 643. Period 652 from $t_E$-$t_I$ may refer to a steady-state sub-phase corresponding to the cycle 644. Period 653 from $t_I$-$t_B$ may refer to an acquisition sub-phase corresponding to the cycle 644. The scan 645 may include an acquisition phase including the acquisition sub-phases 647, 649, 651, and 653. The scan 645 may include a steady-state phase including the steady-state sub-phases 646, 648, 650, and 652. The steady-state phase may include a first number (count) of TRs in each of which the steady-state sequence may be applied. The acquisition phase may include a second number (count) of TRs in each of which the acquisition sequence may be applied.

In some embodiments, the processing device 140 may determine whether to trigger the acquisition phase of the scan using a gating technique, such as respiration gating, electrocardiogram (ECG) gating, pulse gating, etc.

In some embodiments, the processing device 140 may obtain a physiological signal of the object during the scan. The physiological signal may include a respiration signal, an ECG signal, and a pulse signal, etc. In some embodiments, a physiological signal acquisition device may acquire the physiological signal of the object. The processing device 140 may obtain the physiological signal from the physiological signal acquisition device.

In some embodiments, an amplitude of the physiological signal may indicate a motion phase of the physiological motion. For example, the amplitude of the respiration signal may represent pressures of the lungs of the object at different times of the scan, volumes of the lungs of the object at different times of the scan, expiratory volumes at different times of the scan, or inspiratory volumes at different times of the scan, etc., which may indicate a respiration phase of the respiratory motion, such as an expiration phase and an inspiration phase. As another example, the amplitude of the ECG signal and/or the pulse signal may represent a voltage of the ECG signal and/or the pulse signal, which may indicate a cardiac phase of the cardiac motion, such as diastole and systole.

Merely by way of example, a trigger process for determining whether to trigger the acquisition phase in a cycle of the physiological motion may be described below. In some embodiments, the trigger process may be applied to at least one of the one or more cycles of the physiological motion.

In some embodiments, the processing device 140 may determine whether the acquisition phase needs to be triggered in the cycle (e.g., whether the acquisition sub-phase of the acquisition phase corresponding to the cycle needs to be triggered) based on the physiological signal. In response to determining that the corresponding acquisition sub-phase does not need to be triggered, the processing device 140 may cause the scanner 110 to operate based on the steady-state sequence. The steady-state sequence may be used to maintain a steady-state spin magnetization in an object. In response to determining that the corresponding acquisition sub-phase needs to be triggered, the processing device 140 may cause the scanner 110 to operate based on the acquisition sequence.

In some embodiments, the processing device 140 may set a trigger condition. When detecting that at least one portion of the physiological signal satisfies the trigger condition, the processing device 140 may initiate an acquisition sub-phase immediately or after a period of time (also referred to as a delay time, abbreviated to TD). In some embodiments, in a cycle, the time outside the acquisition sub-phase may be deemed the corresponding steady-state sub-phase. As used herein, "immediately" suggests that an acquisition sub-phase is initiated within a short period of time, e.g., less than 30 seconds, or 20 seconds, or 10 seconds, or 5 seconds, or 1 second, from the detection that at least one portion of the physiological signal satisfies the trigger condition. In some embodiments, the TD may be 5 seconds, 10 seconds, 30 seconds, 1 minute, more, from the detection that at least one portion of the physiological signal satisfies the trigger condition. In a cycle, the at least one portion of the physiological signal that satisfies the trigger condition may be referred to as a reference portion or a trigger portion.

In some embodiments, the trigger condition may relate to an amplitude and/or an acquisition time of the reference portion, when the reference portion is detected within a cycle of a physiological motion, etc. For instance, the trigger condition may include that an amplitude of the reference portion is within an amplitude range, the reference portion is acquired within a time range of the cycle of the physiological motion, or the like, or any combination thereof. For example, if the acquired physiological signal is the ECG signal, the reference portion may be one portion of the ECG signal that represents an R wave of the ECG signal in the cycle.

Figure 7:
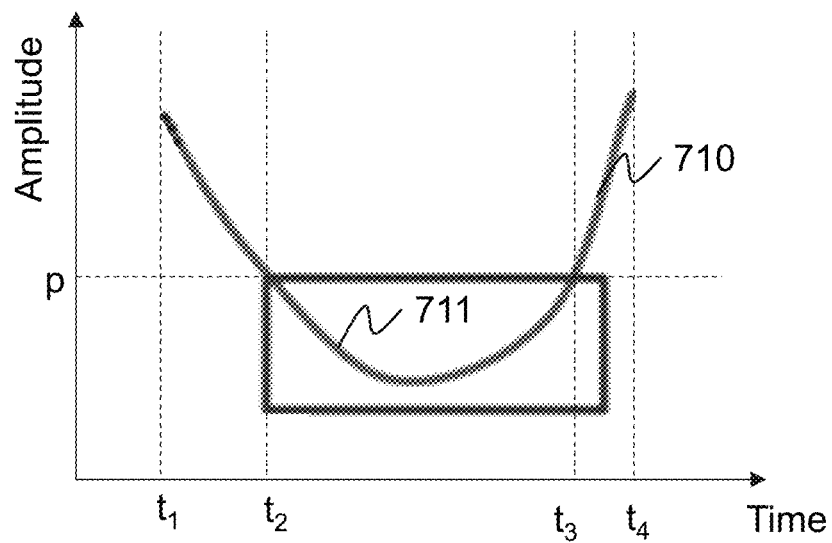
FIG. 7 is a schematic diagram illustrating an exemplary respiration curve in one cycle of respiration of an object according to some embodiments of the present disclosure.

FIG. 7 is a schematic diagram illustrating an exemplary respiration curve in one cycle of respiration of an object according to some embodiments of the present disclosure. A curve 710 shown in FIG. 7 may represent a relation between an acquisition time and an amplitude of a respiration signal of the object acquired in one cycle (e.g., a period from $t_1$ to $t_4$) of respiration of the object. As shown in FIG. 7, the vertical axis of the curve 710 represents the amplitude of the acquired respiration signal that indicate a respiration state (e.g., an expiration phase or an inspiration phase). For example, in the curve 710, the amplitude of the acquired respiration signal may represent the pressures of the lungs of the object at different times in the period from $t_1$ to $t_4$. The greater the amplitude of the respiration signal is, the greater the pressure of the lungs of the object at the acquisition time corresponding to the respiration signal may be. A portion of the curve 710 of which the amplitude decreases over time may indicate the expiration phase of the object, and a portion of the curve 710 of which the amplitude increases over time may indicate the inspiration phase of the object. As shown in FIG. 7, the corresponding acquisition sub-phase may include a period from $t_2$ to $t_3$. The corresponding steady-state sub-phase may include a period from $t_1$ to $t_2$ and a period from $t_3$ to $t_4$. The corresponding acquisition sub-phase may include the end of the expiration phase. The amplitude of the respiration signal acquired in the corresponding acquisition sub-phase may be less than or equal to an amplitude threshold, e.g., the value p in FIG. 7. The amplitude of the respiration signal acquired in the corresponding steady-state sub-phase may be greater than the amplitude threshold. Curve 711 in a rectangle in FIG. 7 may be a portion of the curve 710 during the corresponding acquisition sub-phase.

In some embodiments, the acquisition sequence and the steady sequence may include pulse information of at least one pulse, such as an RF pulse (e.g., an excitation RF pulse), and/or a magnetic field gradient (e.g., a slice selection gradient, a readout gradient, a phase encoding gradient, a dephasing gradient, etc.). Pulse information of a pulse may include a waveform of the pulse, timing information (e.g., indicating the time to start to impose the pulse) of the pulse, a flip angle of the pulse, a direction along which the pulse is imposed, or the like, or any combination thereof. In some embodiments, the acquisition sequence and the steady sequence may be different in applying one or more magnetic field gradients. The one or more magnetic field gradients may include a slice selection gradient, a readout gradient, a phase encoding gradient, a dephasing gradient, or the like, or any combination thereof.

In some embodiments, the acquisition sequence may include a first excitation RF pulse with a flip angle. The first excitation RF pulse may be configured to tip a portion of the longitudinal magnetization of the object into the transverse plane. The flip angle may refer to the rotation of the net magnetization vector by an RF pulse (e.g., the first excitation RF pulse) relative to the main magnetic field. In some embodiments, the flip angle of the first excitation RF pulse may be any value. For example, the flip angle of the first excitation RF pulse may be equal to or less than 90°.

In some embodiments, the acquisition sequence may include a first slice selection gradient. The first slice selection gradient may be imposed along a first direction perpendicular to a plane of one or more target slices of the object, resulting in a linear variation of potential resonance frequencies in the first direction. For example, if the plane of the one or more target slices of the object is parallel to the plane XY in FIG. 1, the first slice selection gradient may be imposed along the Z direction in FIG. 1. The first excitation RF pulse may be a tailored RF pulse, of which the frequency components may match the range of frequencies included in the one or more target slices. The first slice selection gradient and the first excitation RF pulse may be combined such that the one or more target slices are excited. In some embodiments, the stronger the field intensity of the first slice selection gradient is, the smaller the thickness of the one or more target slices may be.

In some embodiment, the acquisition sequence may include one or more readout gradients (also referred to as frequency encoding gradients) and one or more phase encoding gradients. In some embodiments, the one or more readout gradients may be imposed along a second direction. The one or more phase encoding gradients may be imposed along a third direction. The one or more target slices may include a plurality of voxels of the object. The one or more readout gradients and the one or more phase encoding gradients may spatially encode at least a portion of the plurality of voxels along the second direction and the third direction. In some embodiments, the first direction, the second direction, and the third direction may be perpendicular to each other. For example, if the plane of the one or more target slices of the object is parallel to the plane XY in FIG. 1, the second direction may be the X direction in FIG. 1, and the third direction may be the Y direction in FIG. 1, or the second direction may be the Y direction in FIG. 1, and the third direction may be the X direction in FIG. 1.

After the first excitation RF pulse, under the influence of at least one of the first slice selection gradient, the one or more readout gradients, and the one or more phase encoding gradients, the procession of the protons in the object may be dephased because the main magnetic field is non-uniform. Dephasing of the procession of the protons in the object may affect the phase encoding of the one or more target slices. In some embodiments, the acquisition sequence may include one or more first dephasing gradients configured to reduce or remove the dephasing of the procession of the protons caused by the non-uniformity of the main magnetic field. In some embodiments, the one or more first dephasing gradients may be imposed along at least one of the first direction, the second direction, and the third direction.

In some embodiments, when the processing device 140 causes the scanner 110 to operate based on the acquisition sequence in one TR of the acquisition phase of the scan, the RF coils 203 may output the first excitation RF pulse. If the plane of one or more target slices of the object is parallel to the XY plane in FIG. 1, the Z coils of the gradient coils 202 (as illustrated in FIG. 2) may output the first slice selection gradient. The X coils (or the Y coils) of the gradient coils 202 (as illustrated in FIG. 2) may output the one or more readout gradients, and the Y coils (or the X coils) of the gradient coils 202 (as illustrated in FIG. 2) may output the one or more phase encoding gradients. At least one of the X coils, the Y coils, and the Z coils of the gradient coils 202 may output the one or more first dephasing gradients. According to the acquisition sequence, one or more echoes may be generated in the TR. The one or more echoes may be received by the RF coils 203. The ADC 208 may convert the one or more acquired echoes to digitized data.

In some embodiments, the steady-state sequence may include a second excitation RF pulse that is the same as the first excitation RF pulse, a second slice selection gradient that is the same as the first slice selection gradient, and one or more second dephasing gradients that are configured to reduce or remove the dephasing of the procession of the protons caused by the non-uniformity of the main magnetic field. In some embodiments, the one or more second dephasing gradients may be imposed along the one or more directions (also referred to as dephasing direction) along which the one or more first dephasing gradients are imposed. For example, the one or more first dephasing gradients and the one or more second dephasing gradients may be imposed along the second direction of the readout gradient. In some embodiments, a count of the one or more second dephasing gradients may be equal to or different from a count of the one or more first dephasing gradients.

In some embodiments, the steady-state sequence may be free of any readout gradient and/or any phase encoding gradient. In some embodiments, waveforms of at least one of the one or more second dephasing gradients and at least one of the one or more first dephasing gradients that are imposed along the same dephasing direction may be the same or different.

In some embodiments, in order to make the effect of reducing or removing the dephasing of the one or more first dephasing gradients and the one or more second dephasing gradients consistent, a zeroth moment of the one or more first dephasing gradients may be equal to a zeroth moment of the one or more second dephasing gradients, a zeroth moment of a gradient (e.g., the first dephasing gradient or the second dephasing gradient) may refer to an area under a waveform of the gradient. In some embodiments, the zeroth moment of at least one of the one or more second dephasing gradients and the zeroth moment of at least one of the one or more first dephasing gradients that are imposed along the same dephasing direction may be the same.

In some embodiments, the loudness of noise caused by a gradient (e.g., the readout gradient, the phase encoding gradient, the first dephasing gradient, and the second dephasing gradient) may depend on an effective amplitude and a slew rate of the gradient. The greater the effective amplitude and/or the slew rate of the gradient is, the greater the Lorentz force caused by the gradient may be, and the louder or higher the noise caused by the gradient may be. The effective amplitude may be kept for a period of time (also referred to as an effective amplitude time) in the gradient to realize the function of the gradient (e.g., spatially encoding the one or more target slices of the object, or reducing or removing the dephasing). In some embodiments, the effective amplitude of the gradient may refer to the maximum amplitude of the gradient. The slew rate of the gradient may refer to a ratio of the effective amplitude of the gradient to a climb time of the gradient. The climb time of the gradient may refer to a time period in which the amplitude of the gradient changes from 0 to the effective amplitude.

Figure 8:
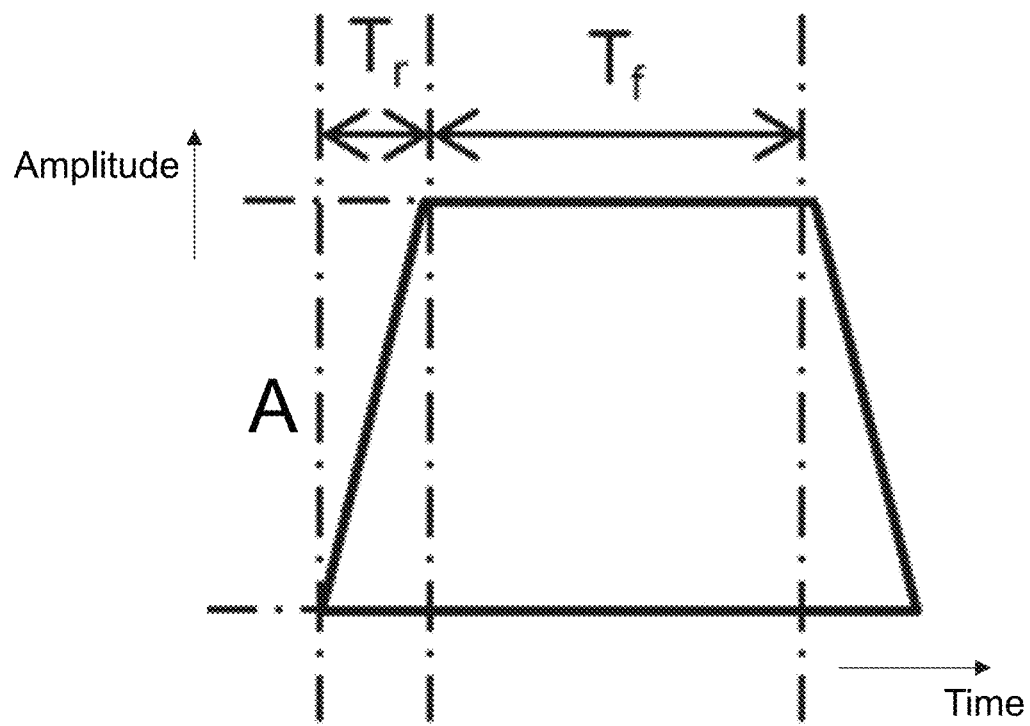
FIG. 8 is a schematic diagram illustrating an exemplary trapezoid gradient according to some embodiments of the present disclosure.

Merely by way of example, FIG. 8 is a schematic diagram illustrating an exemplary trapezoid gradient according to some embodiments of the present disclosure. As shown in FIG. 8, the horizontal axis of a waveform of the gradient 800 may be a time axis. The vertical axis of the waveform of the gradient 800 may represent the amplitude of the gradient 800. The waveform of the gradient 800 may indicate a variation of the amplitude of the gradient 800 over time.

A zeroth moment of the gradient 800 may be represented as Equation (1) below:

$$\text{Moment} = \tfrac{1}{2} A (T_r + 2T_f), \tag{1}$$

wherein Moment refers to the zeroth moment of the gradient 800 that is equal to an area of the gradient 800, A refers to the effective amplitude of the gradient 800, $T_r$ refers to the climb time of the gradient 800, and $T_f$ refers to the effective amplitude time of the gradient 800. According to Equation (1), with the zeroth moment of the gradient 800 unchanged, extending a duration of the gradient may make the effective amplitude A and/or the slew rate of the gradient 800 reduced, which may reduce the noise caused by the gradient 800.

In some embodiments, for a direction (e.g., the first direction, the second direction, or the third direction), a duration of a first dephasing period of the first dephasing gradient may be shorter than a duration of a second dephasing period of the second dephasing gradient. For example, the duration of a second dephasing gradient imposed in a direction (e.g., the first direction, the second direction, or the third direction) may be equal to the TR. An effective amplitude of the second dephasing gradient may be smaller than an effective amplitude of the first dephasing gradient. A slew rate of the second dephasing gradient may be lower than a slew rate of the first dephasing gradient.

In some embodiments, when the processing device 140 causes the scanner 110 to operate based on the steady sequence in one TR of the steady-state phase of the scan, the RF coils 203 may output the second excitation RF pulse. If the plane of one or more target slices of the object is parallel to the XY plane in FIG. 1, the Z coils of the gradient coils 202 (as illustrated in FIG. 2) may output the second slice selection gradient. The X coils and the Y coils of the gradient coils 202 (as illustrated in FIG. 2) may not output any phase encoding gradient and/or any readout gradient. At least one of the X coils, the Y coils, and the Z coils of the gradient coils 202 may output the one or more second dephasing gradients.

Figure 9:
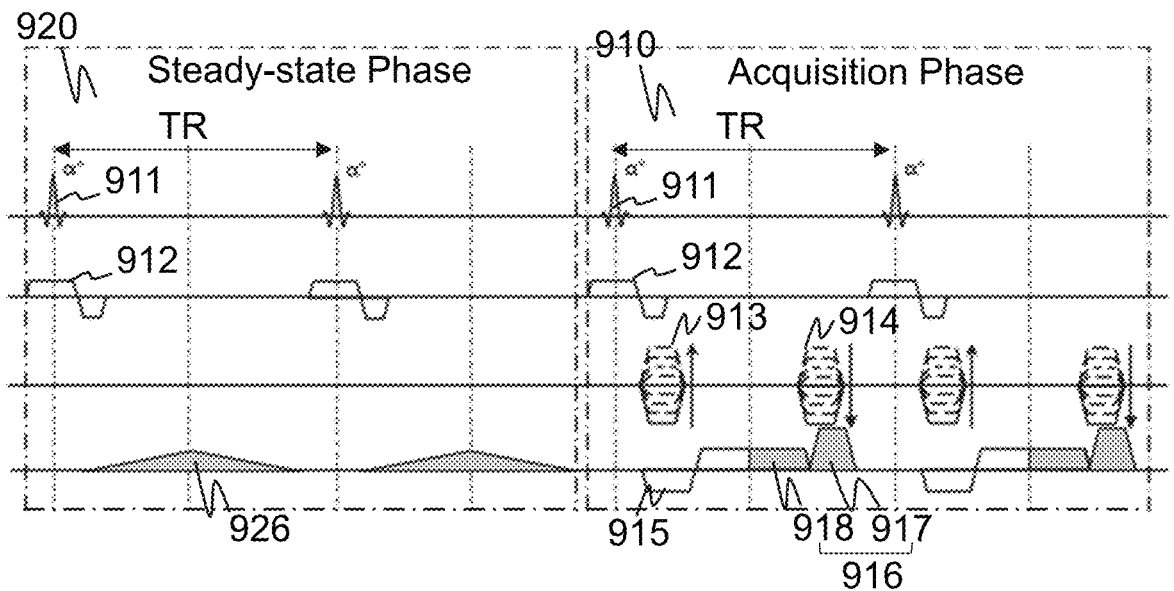
FIG. 9 is a schematic diagram illustrating an exemplary pulse sequence according to some embodiments of the present disclosure.

Merely by way of example, FIG. 9 is a schematic diagram 900 illustrating an exemplary steady sequence and an exemplary acquisition phase according to some embodiments of the present disclosure. As shown in FIG. 9, the acquisition phase may include two TRs. In each of the two TRs, the acquisition sequence 910 may be applied. The acquisition sequence 910 may include an excitation RF pulse 911 with a flip angle α°, a slice selection gradient 912 imposed along the first direction, two phase encoding gradients 913 and 914 imposed along the third direction, a readout gradient 915 imposed along the second direction, and a first dephasing gradient 916 imposed along the second direction. The phase encoding gradient 913 may be configured to spatially encode the one or more target slices of the object. The phase encoding gradients 914 may be configured to eliminate the effects caused by the phase encoding gradient 913. The first dephasing gradient 916 may include a first gradient 917 and a second gradient 918.

As illustrated in FIG. 9, the steady-state phase may include two TRs. In each of the two TRs, the steady sequence 920 may be applied. The steady sequence 920 may include the excitation RF pulse 911 with the flip angle α°, the slice selection gradient 912 imposed along the first direction, and a second dephasing gradient 926 imposed along the second direction. The steady sequence 920 may be free of any phase encoding gradients and free of any readout gradients. The duration of the second dephasing period of the second dephasing gradient 926 may be longer than the duration of the first dephasing period of the first dephasing gradient 916. The effective amplitude of the second dephasing gradient 926 may be smaller than the effective amplitude of the first gradient 917. The slew rate of the second dephasing gradient 926 may be lower than the rates of climb of the first gradient 917 and the second gradient 918. The zeroth moment of the second dephasing gradient 926 (e.g., an area of the second dephasing gradient 926 filled with gray) may be equal to the zeroth moment of the first dephasing gradient 916 (e.g., an area of the first dephasing gradient 916 filled with gray).

In some embodiments, the existence of the excitation RF pulse, the slice selection gradient, and the second dephasing gradient in the steady sequence may make the precession of the protons of the object stable when the scanner 110 operates based on the steady sequence. Compared to the acquisition sequence, when the scanner 110 operates based on the steady sequence, the absence of any phase encoding gradient and/or any readout gradient in the steady sequence may make the scanner 110 generate less noise. Compared to the first dephasing gradient of the acquisition sequence, the second dephasing gradient with the smaller effective amplitude and/or the lower slew rate may further make the scanner 110 generate less noise.

In some embodiments, in the steady-state phase of the scan, the processing device 140 may also cause the scanner 110 to operate based on the acquisition sequence. However, in the steady-state phase of the scan, compared to operating based on the acquisition sequence, when the scanner 110 operates based on the steady sequence according to some embodiments described in the present disclosure, the sound the scanner 110 generates during the scan may be of less loudness and a stronger rhythm, which may make the physiological motion of the object more smooth or stable (e.g., making the object breathe more smoothly), thereby improving the accuracy of the triggering of the acquisition phase based on the physiological signal of the physiological motion and/or reducing motion artifacts in one or more images.

In some embodiments, the acquired MR data may be filled into k-space based on the pulse sequence. As used herein, the MR data used to be filled into the k-space may refer to the MR data acquired in the acquisition phase. In some embodiments, the acquired MR data may be filled into the k-space based on the acquisition sequence of the pulse sequence. In some embodiments, a plurality of echoes may be acquired in the scan. The ADC 208 may convert the plurality of acquired echoes from analog signals to digitized data (e.g., digitized echoes). The digitized echoes may be filled into the k-space based on the acquisition sequence of the pulse sequence.

In some embodiments, according to the one or more readout gradients and the one or more phase encoding gradients applied in the acquisition phase of the scan, phase information and frequency information may be encoded in the acquired echoes. The digitized echoes may be filled into the k-space based on the phase information and the frequency information.

In some embodiments, the Kx axis of the k-space (e.g., as shown in FIG. 10A and FIG. 10B) may represent phase encoding of the MR data, and the Ky axis of the k-space (e.g., as shown in FIG. 10A and FIG. 10B) may represent frequency encoding of the MR data. A manner in which the plurality of echoes is sampled to be filled into the k-space may be referred to as a k-space trajectory. The k-space trajectory may include a Cartesian trajectory and a non-Cartesian trajectory. In the Cartesian trajectory, each of the digitized echoes may fill a line of the k-space along the Kx direction of the k-space. The line of the k-space may be along the Ky direction of the k-space. The non-Cartesian trajectory may include a spiral trajectory, a radial trajectory, a zig-zag trajectory, etc.

In some embodiments, as used in the present disclosure, data in the k-space corresponding to an echo may be referred to as a data line. In some embodiments, the plurality of echoes may be filled into the k-space in a linear manner or a segmented manner. In the linear manner, the data lines corresponding to the plurality of echoes may be distributed in the k-space in an order in which the plurality of echoes are acquired.

In some embodiments, when the scan is performed during two or more cycles of the physiological motion of the object, the plurality of echoes may be filled into the k-space based on a segmented manner. In the segmented manner, the k-space may be divided into a plurality of regions based on a count of echoes acquired in each of the two or more cycles. For example, if 4 echoes are acquired in each of the two or more cycles, the k-space may be divided into 4 regions. The echoes acquired in different cycles of the two or more cycles may be filled in same regions of the plurality of regions. The echoes acquired in a same cycle of the two or more cycles may be filled in different regions of the plurality of regions. In some embodiments, each of the plurality of echoes acquired in each of the two or more cycles may correspond to a motion phase of the physiological motion of the object. The motion phase corresponding to an echo may indicate a motion state of the physiological motion of the object during the acquisition time of the echo. The echoes corresponding to a same motion phase may be filled into a same region of the plurality of regions.

Merely by way of example, the scan may be performed during two or more cycles of the physiological motion of the object, and n echoes may be acquired and filled into the k-space based on the Cartesian trajectory. In each of the two or more cycles of the physiological motion, 4 of the n echoes may be acquired.

FIG. 10A is a schematic diagram illustrating an exemplary linear manner in which echoes are filled into k-space based on a Cartesian trajectory according to some embodiments of the present disclosure. As shown in FIG. 10A, each of the n echoes may be filled into one of n lines of the k-space (e.g., line 1, line 2, line 3, . . . , line n) along the positive (e.g., from left to right of FIG. 10A) or negative (e.g., from right to left of FIG. 10A) Kx direction shown in FIG. 10A according to the acquisition order of the n echoes. A line of the k-space may be along the Ky direction of the k-space shown in FIG. 10A. The Ky direction may relate to the phase encoding of the n echoes, and the Kx direction may relate to the frequency encoding of the n echoes. For example, as shown in FIG. 10A, the first-acquired echo 1011 may be filled into line 1, the second-acquired echo 1012 may be filled into line 2, the third-acquired echo 1013 may be filled into line 3, the fourth-acquired echo 1014 may be filled into line 4, and so on.

FIG. 10B is a schematic diagram illustrating an exemplary segmented manner in which echoes are filled into k-space based on a Cartesian trajectory according to some embodiments of the present disclosure. As shown in FIG. 10B, each of the n echoes may be filled into one of n lines of the k-space (e.g., line 1, line 2, line 3, . . . , line n) along the positive (e.g., from left to right of FIG. 10B) or negative (e.g., from right to left of FIG. 10B) Kx direction shown in FIG. 10A. A line (also referred to as a phase encoding line) of the k-space may be along the Ky direction of the k-space shown in FIG. 10B. The Ky direction and the Kx direction in FIG. 10B may be the same as those in FIG. 10A.

The k-space may be divided into 4 regions 1025-1028. As illustrated, the n lines of the k-space to be filled with the n echoes may be indicated by the lines filled with different colors (e.g., black, gray, or the like). The lines filled with a same color may be in different regions, while the lines filled with different colors may be in a same region. Echoes from the same cycle may be filled in the positions of the lines with a same color. Echoes from different cycles but corresponding to a same motion phase of the physiological motion may be filled into a same region. Mere by way of example, the echoes including echoes 1021-1024 from the first cycle may be filled into the lines with the black color along the positive Kx direction according to the acquisition order of the echoes 1021-1024. For example, the first-acquired echo 1021 may be filled into the black line in region 1025 (e.g., line 1), the second-acquired echo 1022 may be filled into the black line in region 1026, the third-acquired echo 1023 may be filled into the black line in region 1027, and the fourth-acquired echo 1024 may be filled into the black line in region 1028. Echoes of other cycles may be filled into the regions in the same way. For example, the echoes from the second cycle may be filled into the lines with the same color as line 2 in regions 1025-1028, and the echoes from the third cycle may be filled into the lines with the same color as line 3 in regions 1025-1028, and the echoes from the last cycle may be filled into the lines with the same color with line n in regions 1025-1028.

In some embodiments, if the physiological signal are used to trigger the acquisition phase of the scan, each of the 4 echoes acquired in each cycle may correspond to a portion of a curve of the physiological signal. The portion of the curve of the physiological signal may represent a motion phase of the physiological motion during the acquisition time of the echo. The data line corresponding to the echo may also correspond to the portion of the curve of the physiological signal. A sequence, along a certain direction (e.g., the Kx direction of the k-space), of the motion phases (or the corresponding portions of the curve of the physiological signal) of the data lines in the k-space may be referred to as a motion modulation form of the k-space.

For example, if the curve 710 in FIG. 7 is used to trigger the acquisition phase of the scan, each of the 4 echoes acquired in each cycle may correspond to a portion of the curve 711 of the curve 710 (e.g., corresponding to a motion phase of the physiological motion). After the n echoes are filled into the k-space, along the Kx direction, the motion modulation form of the k-space in FIG. 10A may be represented as pattern 1015. The motion modulation form 1015 may include a plurality of waves each of which corresponds to the curve 711. For example, a shape of each of the plurality of waves of pattern 1015 may be similar to the curve 711. A count of the plurality of waves may be equal to the count of the two or more cycles.

Along the Kx direction, the motion modulation form of the k-space in FIG. 10B may be represented as pattern 1029. Because the data lines in the same region correspond to the same motion phase (e.g., the data lines in the same region correspond to the same portion of the curve 711), the motion modulation form 1029 may be in a form of steps. The tendency (e.g., the dashed line 1030 in FIG. 10B) of the motion modulation form 1029 may be similar to the curve 711. Therefore, the motion modulation form 1029 may be regarded as including one wave corresponding to the curve 711. A side lobe of the motion modulation form with one wave may be smaller than a side lobe of the motion modulation form with a plurality of waves, and a point spread function of the motion modulation form with one wave may be better than a point spread function of the motion modulation form with a plurality of waves, which may suppress the motion artifacts in one or more images.

In some embodiments, the segmented manner may also be applied in a scan that is performed during one or more cycles of the physiological motion of the object and without the steady-state phase.

In 620, the processing device 140 (e.g., the image generation module 520) may generate one or more images of the object based on the MR data.

If the TR of the scan is much shorter than each cycle of the physiological motion (e.g., the TR is $\frac{1}{10}$, $\frac{1}{20}$, $\frac{1}{50}$, $\frac{1}{100}$, etc., of each cycle of the physiological motion), a duration of the acquisition phase may also be much shorter than each cycle of the physiological motion. In this case, the steady sequence may be applied in the steady-state phase of the scan to make the procession of the protons of the object stable in the steady-state phase and reduce the noise caused by the scanner 110 in the steady-state phase.

For example, in a gradient echo sequence, an excitation RF pulse with a relatively small flip angle may be applied, and so the TR may be short. For example, the TR corresponding to a three-dimensional (3D) gradient echo sequence may be within 30 milliseconds (ms). As another example, the TR corresponding to a two-dimensional (2D) gradient echo sequence may be within 300 ms. A cycle of a person's respiration may be 3000-8000 ms, which is much longer than the TR corresponding to the gradient echo sequence. When the acquisition sequence that is a gradient echo sequence is applied in the acquisition phase to acquire one or more echoes, the steady sequence described in the present disclosure may be applied in the steady-state phase to make the procession of the protons of the object stable in the steady-state phase and reduce the noise caused by the scanner 110 in the steady-state, thereby reducing motion artifacts in one or more images. As another example, when the acquisition sequence that is a fast spin echo (FSE) sequence corresponding to a relatively short TR is applied in the acquisition phase to acquire one or more echoes, the stead sequence described in the present disclosure may be applied in the steady-state phase.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

EXAMPLES

The following examples are provided for illustration purposes and not intended to be limiting.

FIG. 11A is a schematic diagram illustrating an exemplary liver image generated based on MR data filled into k-space in a linear manner according to some embodiments of the present disclosure. FIG. 11B is a schematic diagram illustrating an exemplary liver image generated based on MR data filled into k-space in a segmented manner according to some embodiments of the present disclosure. The image 1100-1 and the image 1100-2 are liver images of a same object. As shown, the image 1100-2 are clearer than the image 1100-1. A first portion of the image 1100-2 in the box 1120 and a second portion of the image 1100-1 in the box 1110 correspond to same tissue of the object. The first portion is clearer than the second portion.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C #, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claimed subject matter may lie in less than all features of a single foregoing disclosed embodiment.

What is claimed is:

1. A system for magnetic resonance imaging (MRI), comprising:
    at least one storage device including a set of instructions; and
    at least one processor in communication with the at least one storage device, wherein when executing the set of instructions, the at least one processor is directed to cause the system to perform operations including:
        causing, based on a pulse sequence, a magnetic resonance (MR) scanner to perform a scan on an object, wherein
            the pulse sequence includes a steady-state phase and an acquisition phase that is different from the steady-state phase, and the steady-state phase and the acquisition phase are periodically distributed in the pulse sequence;
            MR data of the object is acquired in the acquisition phase, and the acquisition phase includes a first dephasing gradient;
            no MR data is acquired in the steady-state phase, and the steady-state phase includes a second dephasing gradient, wherein a maximum amplitude of the first dephasing gradient is greater than a maximum amplitude of the second dephasing gradient or a slew rate of the first dephasing gradient is greater than a slew rate of the second dephasing gradient; and
        generating one or more images of the object based on the MR data.

2. A system for magnetic resonance imaging (MRI), comprising:
    at least one storage device including a set of instructions; and
    at least one processor in communication with the at least one storage device, wherein when executing the set of instructions, the at least one processor is directed to cause the system to perform operations including:
        causing, based on a pulse sequence, a magnetic resonance (MR) scanner to perform a scan on an object, wherein
            the pulse sequence includes a steady-state phase and an acquisition phase that is different from the steady-state-phase, and the steady-state phase and the acquisition phase are periodically distributed in the pulse sequence;
            MR data of the object is acquired in the acquisition phase, and the acquisition phase includes a first dephasing gradient;
            no MR data is acquired in the steady-state phase, and the steady-state phase includes a second dephasing gradient, wherein
                the acquisition phase includes a phase encoding gradient and a readout gradient, while the steady-state phase is free of at least one of any phase encoding gradient or any readout gradient; or
                a duration of a first dephasing period of the first dephasing gradient is shorter than a duration of a second dephasing period of the second dephasing gradient; and
        generating one or more images of the object based on the MR data.

3. A system for magnetic resonance imaging (MRI), comprising:
    at least one storage device including a set of instructions; and
    at least one processor in communication with the at least one storage device, wherein when executing the set of instructions, the at least one processor is directed to cause the system to perform operations including:
        causing, based on a pulse sequence, a magnetic resonance (MR) scanner to perform a scan on an object during multiple cycles of a physiological motion of the object;

acquiring MR data of the object by filling echoes acquired in the multiple cycles into k-space based on the pulse sequence, wherein the pulse sequence includes a steady-state phase and an acquisition phase that is different from the steady-state phase, no MR data being acquired in the steady-state phase, and the steady-state phase and the acquisition phase being periodically distributed in the pulse sequence;

the k-space is divided into a plurality of regions based on a count of the echoes acquired in each of the multiple cycles, the echoes acquired in each of the multiple cycles corresponding to a portion of the MR data acquired in the acquisition phase;

the echoes acquired in different cycles of the multiple cycles are filled in same regions of the plurality of regions; and the echoes acquired in a same cycle of the multiple cycles are filled in different regions of the plurality of regions; and generating one or more images of the object based on the MR data.

4. The system of claim 1, wherein the acquisition phase includes an excitation pulse and a spatial encoding gradient including at least one of a slice selection gradient, a phase encoding gradient, or a readout gradient; and the steady-state phase includes the excitation pulse or the slice selection gradient.

5. The system of claim 4, wherein the steady-state phase is free of at least one of any phase encoding gradient or any readout gradient.

6. The system of claim 4, wherein the second dephasing gradient or the first dephasing gradient is applied along at least one of a direction of the slice selection gradient, a direction of the phase encoding gradient, or a direction of the readout gradient.

7. The system of claim 1, wherein a zeroth moment of the second dephasing gradient is equal to a zeroth moment of the first dephasing gradient, and the zeroth moment of the first dephasing gradient or the zeroth moment of the second dephasing gradient refers to an area under a waveform of the first dephasing gradient or the second dephasing gradient.

8. The system of claim 1, wherein a duration of a first dephasing period of the first dephasing gradient is shorter than a duration of a second dephasing period of the second dephasing gradient.

9. The system of claim 1, wherein the scan is performed during multiple cycles of a physiological motion of the object;

the steady-state phase includes one or more steady-state sub-phases;

the acquisition phase includes one or more acquisition sub-phases; and each of the multiple cycles corresponds to a pair of a steady-state sub-phase and an acquisition sub-phase.

10. The system of claim 1, wherein the steady-state phase and the acquisition phase correspond to a repetition time (TR) of the scan; and the steady-state phase and the acquisition phase correspond to different magnetic field gradients.

11. The system of claim 2, wherein the acquisition phase or the steady-state phase includes an excitation pulse or a slice selection gradient.

12. The system of claim 11, wherein the second dephasing gradient or the first dephasing gradient is applied along at least one of a direction of the slice selection gradient, a direction of the phase encoding gradient, or a direction of the readout gradient.

13. The system of claim 2, wherein a zeroth moment of the second dephasing gradient is equal to a zeroth moment of the first dephasing gradient, and the zeroth moment of the first dephasing gradient or the zeroth moment of the second dephasing gradient refers to an area under a waveform of the first dephasing gradient or the second dephasing gradient.

14. The system of claim 2, wherein a maximum amplitude of the first dephasing gradient is greater than a maximum amplitude of the second dephasing gradient.

15. The system of claim 2, wherein a slew rate of the first dephasing gradient is greater than a slew rate of the second dephasing gradient.

16. The system of claim 2, wherein the scan is performed during multiple cycles of a physiological motion of the object;

the steady-state phase includes one or more steady-state sub-phases;

the acquisition phase includes one or more acquisition sub-phases; and each of the multiple cycles corresponds to a pair of a steady-state sub-phase and an acquisition sub-phase.

17. The system of claim 2, wherein the steady-state phase and the acquisition phase correspond to a repetition time (TR) of the scan; and the steady-state phase and the acquisition phase correspond to different magnetic field gradients.

18. The system of claim 3, wherein each of the echoes acquired in each of the multiple cycles corresponds to a motion phase of the physiological motion of the object; and echoes corresponding to a same motion phase are filled into a same region of the plurality of regions.

19. The system of claim 3, wherein the causing, based on the pulse sequence, the MR scanner to perform a scan on an object includes:

acquiring a physiological signal of the physiological motion of the object;

evaluating a trigger condition based on the physiological signal; and causing the MR scanner to operate based on the evaluation of the trigger condition.

20. The system of claim 19, wherein the causing the MR scanner to operate based on the evaluation of the trigger condition includes:

in response to determining that the trigger condition is not satisfied, causing the MR scanner to operate in the steady-state phase of the scan in which no MR data is acquired; or in response to determining that the trigger condition is satisfied, causing the MR scanner to operate in the acquisition phase of the scan in which the MR data of the object is acquired.

* * * * *